(12) United States Patent
Riel

(10) Patent No.: US 11,877,991 B2
(45) Date of Patent: *Jan. 23, 2024

(54) USE OF COLCHICINE TO INHIBIT TUMOR GROWTH AND METASTASES

(71) Applicant: MURRAY AND POOLE ENTERPRISES LTD, Gibraltar (GI)

(72) Inventor: Michael Riel, Dubai (AE)

(73) Assignee: MURRAY AND POOLE ENTERPRISES LTD, Gibraltar (GI)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,692

(22) Filed: Dec. 26, 2022

(65) Prior Publication Data

US 2023/0137776 A1 May 4, 2023

Related U.S. Application Data

(63) Continuation of application No. 16/966,892, filed as application No. PCT/EP2019/052492 on Feb. 1, 2019, now Pat. No. 11,534,415.

(60) Provisional application No. 62/625,354, filed on Feb. 2, 2018.

(51) Int. Cl.
*A61K 31/16* (2006.01)
*A61K 31/165* (2006.01)
*A61P 35/00* (2006.01)

(52) U.S. Cl.
CPC ............ *A61K 31/165* (2013.01); *A61P 35/00* (2018.01)

(58) Field of Classification Search
CPC .................................................. A61K 31/165
See application file for complete search history.

(56) References Cited

FOREIGN PATENT DOCUMENTS

| CN | 1748671 A | 3/2006 |
|---|---|---|
| CN | 101485637 B | 7/2009 |
| WO | 2014066944 A1 | 5/2014 |
| WO | 2014/170755 A2 | 10/2014 |
| WO | 2015/069770 A1 | 5/2015 |

OTHER PUBLICATIONS

Zu-Yan Lin et al., "Anticancer effects of clinically acceptable colchicine concentrations on human gastric cancer cell lines", The Kaohsiung Journal of Medical Sciences, vol. 32, 2016, pp. 68-73.
Asli Muvaffak et al., "Prolonged Cytotoxic Effect of Colchicine Released from Biodegradable Microspheres", Journal of Biomedical Materials Research Part B: Applied Biomaterials: An Official Journal of The Society for Biomaterials, The Japanese Society for Biomaterials, and The Australian Society for Biomaterials and the Korean Society for Biomaterials, vol. 71, No. 2, pp. 295-304.
International Search Report and Written Opinion, dated May 24, 2019, PCT International Application No. PCT/EP2019/052492, pp. 1-16.
Sreevalli Bokka, "Controlled Release of the Cytarabine and Colchicine Using Hydrogel Derived from the Polymerized Microemulson," Diss. University of Akron, 2015, pp. 1-105.

*Primary Examiner* — Shawquia Jackson
(74) *Attorney, Agent, or Firm* — BioPharma Law Group, PLLC

(57) ABSTRACT

Use of colchicine to inhibit tumor growth and metastases in mammalian subjects comprising the administration of the compositions and formulations are provided. The described colchicine compositions and formulations include rapid release, sustained release, and multi-modal release compositions and formulations suitable for alone or in combination with additional pharmaceutically active agents useful in treating tumor growth and metastases.

22 Claims, 8 Drawing Sheets

USE OF COLCHICINE TO INHIBIT TUMOR GROWTH AND METASTASES

CROSS REFERENCE TO RELATED APPLICATIONS

This application is a continuation of U.S. Nonprovisional application Ser. No. 16/966,892 filed on Aug. 1, 2020, which is a National Stage of International Application No. PCT/EP2019/052492 filed on Feb. 1, 2019, which claims priority to U.S. Provisional Application No. 62/625,354 filed on Feb. 2, 2018. The contents of the above applications are incorporated herein by reference in their entirety.

BACKGROUND

Colchicine, chemical name (−)-N-[(7S,12aS)-1,2,3,10-tetramethoxy-9-oxo-5,6,7,9-tetrahydrobenzo[a]heptalen-7-yl]-acetamide, is an alkaloid found in extracts of *Colchicum autumnale, Gloriosa superba*, and other plants. It is a microtubule-disrupting agent used in the treatment of conditions that may be treated, relieved or prevented with anti-inflammatory treatment.

Colchicine is well recognized as a valid therapy in acute flares of gouty arthritis, familial Mediterranean fever (FMF), and Behçet's disease. Colchicine has also been used to treat many inflammatory disorders prone to fibrosis. In the recent past, colchicine has been proposed to be effective in therapy in cardiovascular diseases.

In particular, colchicine has been proposed as a first treatment option for recurrent pericarditis (class I indication) and optional for acute pericarditis (class IIa indication) in the 2004 European guidelines on the management of pericardial diseases (Maisch et al., "Guidelines on the Diagnosis and Management of Pericardial Diseases," *Eur. Heart. J.*, 2004, 25:916-928).

Imazio et al. (*Circulation*, 2005, 112(13):2012-2016) showed that colchicine was effective for the treatment and the prevention of recurrent pericarditis in a prospective, randomized, open-label designed study of 120 subjects with a first episode of acute pericarditis (idiopathic, viral, postpericardiotomy syndromes, and connective tissue diseases), who were randomly assigned to conventional treatment plus aspirin or conventional treatment plus colchicine (1.0 to 2.0 mg for the first day and then 0.5 to 1.0 mg/day for 3 months). The primary end point was recurrence rate, which was significantly reduced from 32.3% down to 10.7% at 18 months in the colchicine group (p=0.004).

Further, the same group showed that colchicine could be efficient after conventional treatment failure to manage acute pericarditis (Imazio at al., *Arch. Intern. Med.*, 2005, 165 (17):1987-91). In a prospective, randomized, open-label design, 84 consecutive subjects with a first episode of recurrent pericarditis were randomly assigned to receive conventional treatment with aspirin alone or conventional treatment plus colchicine (1.0-2.0 mg the first day and then 0.5-1.0 mg/d for 6 months). The primary end point was the recurrence rate, which was significantly decreased in the colchicine group (actual rates at 18 months were 24.0% vs 50.6% with conventional treatment).

It has also been shown that colchicine is effective for secondary prevention of recurrent pericarditis Imazio et al., *Ann. Intern. Med.*, 2011, 155(7):409-14). Colchicine has also been proposed to reduce postpericardiotomy reactions revealed as pericarditis (Imazio et al., *Am. Heart J.*, 2011, 162(3):527-532; and Meurin and Tabet, *Arch. Cardiovasc. Dis.*, 2011, 104(8-9):425-427).

Colchicine for the treatment of post-pericardiotomy syndrome (PPS) was tested for the first time in a preliminary prospective, open-label, randomized trial of colchicine (1.5 mg/day) compared with placebo beginning on the third post-operative day in 163 subjects who underwent cardiac surgery (Finkelstein et al., *Herz*, 2002, 27:791-194).

The effectiveness of colchicine for the prevention of PPS has also been shown in a multicentre, double-blind, randomized trial, in which 360 subjects (mean age 65.7+12.3 years, 66% males), 180 in each treatment arm, were randomized to receive placebo or colchicine (1.0 mg twice daily for the first day followed by a maintenance dose of 0.5 mg twice daily for 1 month in subjects ≥70 kg, and halved doses for subjects, 70 kg or intolerant to the highest dose) on the third post-operative day (Imazio et al., *Eur. Heart J.*, 2010, 31:2749-2754).

In another study, the effectiveness of colchicine was shown for cardiovascular disease. In this clinical trial with a prospective, randomized, observer-blinded endpoint design, 532 subjects with stable coronary disease receiving aspirin and/or clopidogrel (93%) and statins (95%) were randomly assigned colchicine 0.5 mg/day or no colchicine and followed for a median of 3 years (Nidorf et al., *JACC*, 2013, 61(4):404-410). This study showed that colchicine 0.5 mg/day administered in addition to statins and other standard secondary prevention therapies appeared effective for the prevention of cardiovascular events in subjects with stable coronary disease.

For the treatment of gout, the recommended dose of colchicine (COLCRYS®) is 1.8 mg/day in one or multiple doses in one hour. For adults with gout, treatment is initiated with a dose of 1.2 mg at the first sign of symptoms followed by 0.6 mg one hour later. (Physician's Desk Reference, 68th ed., 2014).

In addition, colchicine has been widely used to ameliorate immune-mediated diseases, and beneficial effects were reported in the treatment of psoriatic arthritis (Seidemann et al., *J. Rheumatol.*, 14:777-779, 1987) and leukocyte-cytoclastic vasculitis (J. P. Callen, *J. Am. Acad. Dermatol.*, 13:193-200, 1987). Moreover, other studies have showed that colchicine inhibits leukocyte-endothelial cell adhesion (Rosenman et al., *F.A.S.E.B. J.*, 5:1603-1609, 1991) and T cell activation (Mekory et al *Cell. Immunol.*, 120:330-340, 1989) by binding to intracellular tubulin monomers that prevents their polymerization (Borisy et al., *J. Cell. Biol.*, 34:533-548, 1967). Thus, colchicine has the potential to impair the process of antigen recognition and may inhibit the cancer cell growth. However, antimitotic colchicine is used only in research due to its known toxicity.

In fact, colchicine is associated with many adverse side effects. COLCRYS®, for instance, is an immediate release formulation of colchicine. Reported adverse effects associated with the administration of COLCRYS® include, but are not limited to, nausea, vomiting, abdominal pain, diarrhea, hair loss, weakness, nerve irritation, severe anemia, low white blood counts, and low platelets (Physician's Desk Reference, 68th ed., 2014).

Solutions to these issues surrounding colchicine toxicity and dosage, as well as other issues are described herein by providing modified formulations of colchicine characterized by a sustained release of an active ingredient, i.e. colchicine. Additionally provided is an effective, once-daily dosage form of colchicine or salts thereof, which improves subject compliance and also reduces some of the known toxic side effects of colchicine compared to the current or higher daily doses of immediate release colchicine formulations.

Additionally, the need for safer and more effective cancer treatments are provided herein that serve either as a single agent that inhibits, reduces, suppresses, prevents, slows, or delays the progression of, shrinks, or directly attacks tumor cells, or that can act in combination with other immune modulating therapies to enhance their therapeutic activity. In particular, colchicine was shown to play a role in the infiltration, maturation and organization of immune cells and macrophage that either promote or inhibit tumor growth, which can contribute to development of effective methods for reducing tumor growth and metastases in a subject with cancer.

BRIEF SUMMARY

In one embodiment, there is provided herein a method for inhibiting, delaying, or reducing tumor growth, or tumor metastases, or tumor growth and tumor metastases, in a subject diagnosed with or believed to be suffering from cancer, comprising administering to the subject an effective amount of, a sustained release formulation comprising up to 0.60 mg colchicine to a subject, said subject optionally being a human subject.

Also disclosed herein there is provided a method for inhibiting, delaying, or reducing tumor growth, or tumor metastases, or tumor growth and tumor metastases, in a subject diagnosed with, or believed to be suffering from cancer, comprising administering to the subject an effective amount of, a sustained release formulation comprising up to 0.60 mg colchicine to a human subject, and a pharmaceutically or biologically effective amount of at least one other immune modulating therapy.

In some embodiments, the immune modulating therapy is one or more of a cancer vaccine, an immunostimulatory agent, adoptive T cell or antibody therapy, and immune checkpoint blockade. In some embodiments, the immune modulating agent is one or more of interleukins, cytokines, chemokines, and antagonists of immune checkpoint blockades. In some embodiments, the immune modulating therapy is a cancer therapy. In some embodiments, the cancer therapy is one or more of surgery or surgical procedures, radiation therapy, and chemotherapy. In some embodiments, colchicine and the immune modulating agent or immune modulating therapy are administered separately. In some embodiments, colchicine and the immune modulating agent or immune modulating therapy are administered concurrently.

BRIEF DESCRIPTION OF THE DRAWINGS/FIGURES

Figure 6:
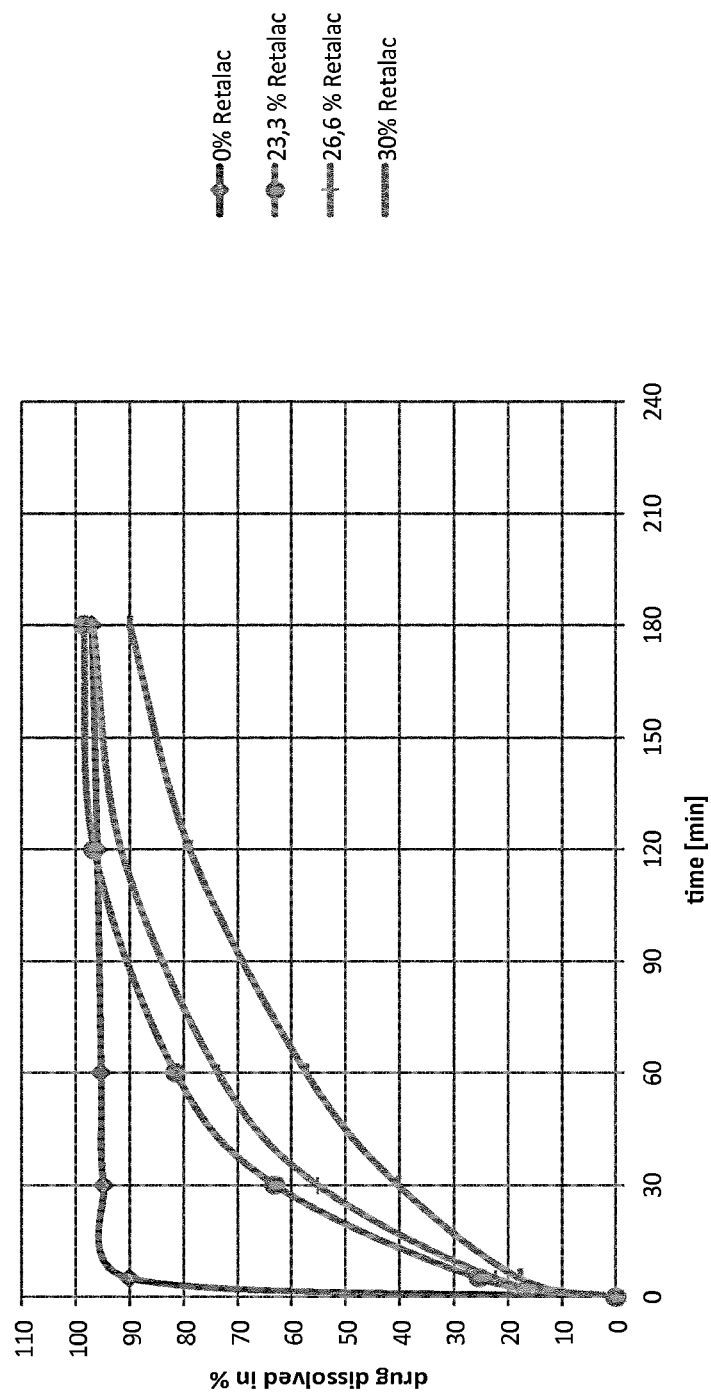
FIG. 6 shows the dissolution profile for colchicine formulation containing 0%, 23.3%, 26.6% and 30% of an exemplary retarding agent.

FIGS. 7A, 7B, 7C, and 7D show plasma colchicine levels (ng/mL) as a function of time (hrs) for colchicine formulations according to FIG. 6.

Figure 8:
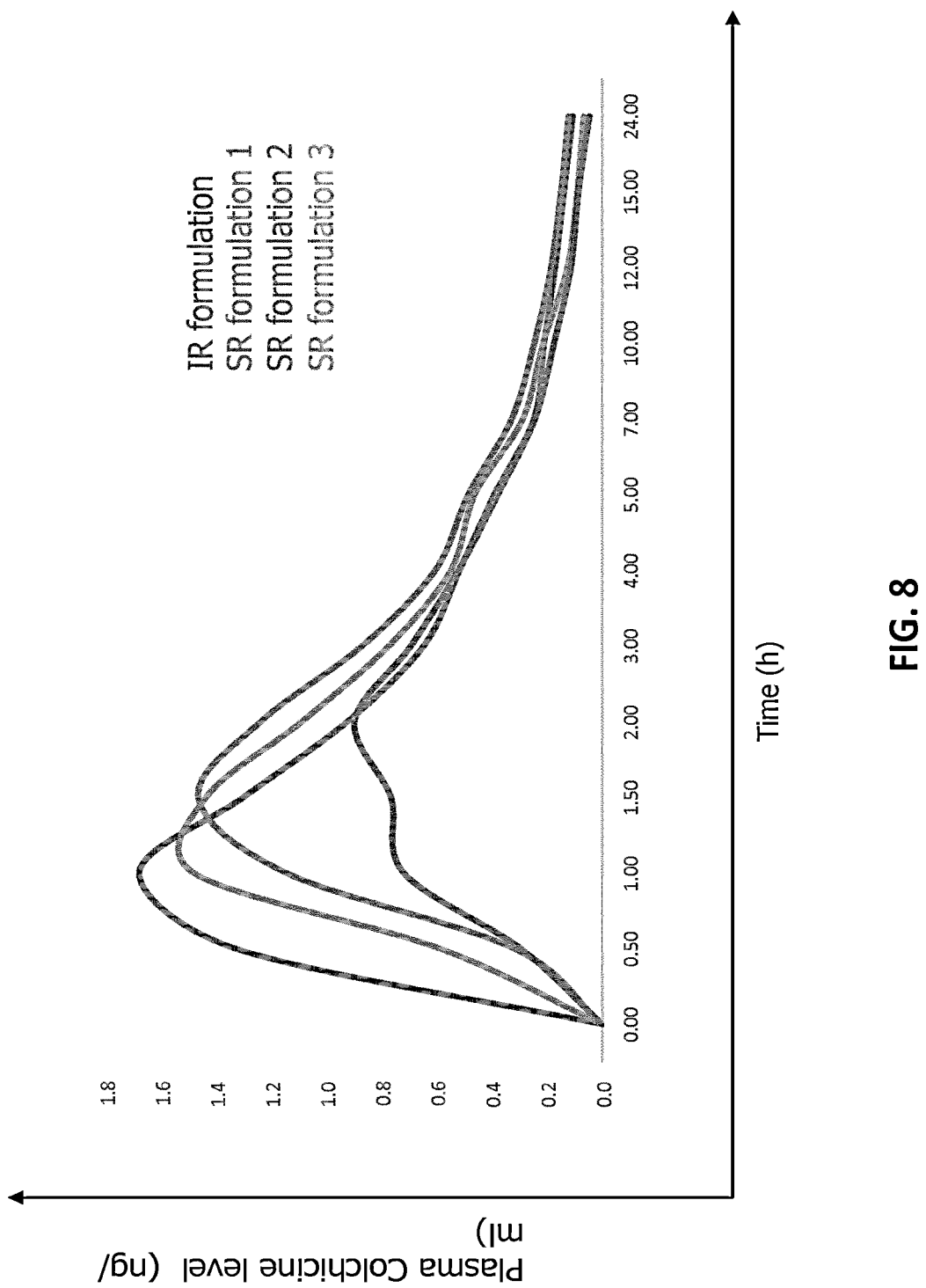

FIG. 8 shows plasma colchicine levels (ng/mL) as a function of time (hrs) for colchicine formulations according to FIG. 6.

DETAILED DESCRIPTION OF THE INVENTION

I. Definitions

For the purposes of the present disclosure, the term "colchicine" includes colchicine and any pharmaceutically acceptable salt thereof.

The phrase "pharmaceutically acceptable" as used herein means that which is generally safe, non-toxic and neither biologically nor otherwise undesirable and includes that which is acceptable for veterinary use as well as human pharmaceutical use.

The phrase "pharmaceutically acceptable salts" as used herein include derivatives of colchicine, wherein the colchicine is modified by making acid or base addition salts thereof, and further refers to pharmaceutically acceptable solvates, including hydrates, and co-crystals of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the colchicine. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparaginate, glutamate, and the like; and combinations comprising one or more of the foregoing salts; organic amine salts such as triethylamine salt, pyridine salt, picoline salt, ethanolamine salt, triethanolamine salt, dicyclohexylamine salt, N,N' dibenzylethylenediamine salt, and the like; and amino acid salts such as arginate, asparaginate, glutamate, and the like; and combinations comprising one or more of the foregoing salts. All forms of such derivatives of colchicine are contemplated herein, including all crystalline, amorphous, and polymorph forms. Specific colchicine salts contemplated herein include colchicine hydrochloride, colchicine dihydrochloride, and co-crystals, hydrates or solvates thereof.

The phrase "pharmacokinetic parameters" as used herein describe the in vivo characteristics of an active agent (or a metabolite or a surrogate marker for the active agent) over time, such as plasma concentration (C), $C_{max}$, $C_n$, $C_{24}$, $T_{max}$, and AUC. The term "$C_{max}$" as used herein is the measured plasma concentration of the active agent at the point of maximum, or peak, concentration. The term as used herein is the measured plasma concentration of the active agent at the point of minimum concentration. The term "$C_n$" as used herein is the measured plasma concentration of the active agent at about n hours after administration. The term "$C_{24}$" as used herein is the measured plasma concentration of the active agent at about 24 hours after administration. The term "$T_{max}$" as used herein refers to the time at which the measured plasma concentration of the active agent is the highest after administration of the active agent. "AUC" is the area under the curve of a graph of the measured plasma concentration of an active agent vs. time, measured from one time point to another time point. For example, the term "$AUC_{0-t}$" as used herein is the area under the curve of plasma concentration versus time from time 0 to time t, where t can be the last time point with measurable plasma concentration for an individual formulation. The term "$AUC_{0-\infty}$," as used herein, or "$AUC_{0-INF}$" as used herein is the calculated area under the curve of plasma concentration versus time from time 0 to time infinity. In steady-state studies, the term "$AUC_{0-\tau}$" as used herein is the area under the curve of plasma concentration over the dosing interval (i.e., from time 0 to time $\tau$ (tau), where tau is the length of the dosing interval. Other pharmacokinetic parameters are the parameter Ke or Kel, the terminal elimination rate constant calculated from a semi-log plot of the plasma concentration versus time curve; $t_{1/2}$ the terminal elimination half-life, calculated as 0.693/Kel; CL/F denotes the apparent total body clearance after administration, calculated as Total Dose/Total $AUC_\infty$; and $V_{area}/F$ denotes the apparent total volume of distribution after administration, calculated as Total Dose/(Total $AUC_\infty \times Kel$).

The term "efficacy" as used herein means the ability of an active agent administered to a subject to produce a therapeutic effect in the subject.

The term "bioavailability" as used herein means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. The term "bioavailability" as used herein can be characterized by one or more pharmacokinetic parameters.

The phrase "dosage form" as used herein means a unit of administration of an active agent. Examples of dosage forms include tablets, capsules, injections, suspensions, liquids, emulsions, creams, ointments, suppositories, inhalable forms, transdermal forms, and the like.

The phrase "immediate release formulation" as used herein refers to a formulation that releases greater than or equal to about 80% of the pharmaceutical agent in less than or equal to about 30 min.

For the purposes of this disclosure, an enhancing agent ("enhancer") is defined as any non-pharmaceutically active ingredient that improves the therapeutic potential of a formulation.

The phrase "sustained release" as used herein is defined herein as release of a pharmaceutical agent in a continuous manner over a prolonged period of time.

By "prolonged period of time" it is meant a continuous period of time of greater than about 1 hour, greater than about 4 hours, greater than about 8 hours, greater than about 12 hours, greater than about 16 hours, or up to more than about 24 hours.

As used herein, unless otherwise noted, the phrase "rate of release" or "release rate" or "dissolution rate" of a drug refers to the quantity of drug released from a dosage form per unit time, e.g., milligrams of drug released per hour (mg/hr) or a percentage of a total drug dose released per hour. Drug release rates for dosage forms are typically measured as an in vitro rate of drug release, i.e., a quantity of drug released from the dosage form per unit time measured under appropriate conditions and in a suitable fluid. The release rates referred to herein are determined by placing a dosage form to be tested in a medium in an appropriate dissolution bath. Aliquots of the medium, collected at pre-set intervals, are then injected into a chromatographic system fitted with an appropriate detector to quantify the amounts of drug released during the testing intervals.

As used herein, the phrase "side effect" refers to a secondary and usually adverse effect of a drug.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric, pancreatic cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, sarcoma, kidney cancer, liver cancer, prostate cancer, vulvar cancer, thyroid cancer, hepatic carcinoma, and various types of head and neck cancers.

The terms "tumor" and "neoplasm" as used herein refer to any mass of tissue that result from excessive cell growth or proliferation, either benign (noncancerous) or malignant (cancerous) including pre-cancerous lesions.

The terms "metastasis," "metastases," "metastatic," and other grammatical equivalents as used herein refer to cancer cells that spread or transfer from the site of origin, e.g., a primary tumor, to other regions of the body with the development of a similar cancerous lesion at the new location. A "metastatic" or "metastasizing" cell as referred to herein is one that loses adhesive contacts with neighboring cells and migrates via the bloodstream or lymph from the primary site of disease to invade neighboring body structures. These terms also refer to the process of metastasis, which includes, but is not limited to detachment of cancer cells from a primary tumor, intravasation of the tumor cells to circulation, their survival and migration to a distant site, attachment and extravasation into a new site from the circulation, and microcolonization at the distant site, and tumor growth and development at the distant site. In certain embodiments, metastatic cancers that are amenable to treatment via the methods provided herein include, but are not limited to metastatic sarcomas, breast carcinomas, ovarian cancer, head and neck cancer, and pancreatic cancer.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug reduces the number of cancer cells; retards or stops cancer cell division, reduces or retards an increase in tumor size; inhibits, e.g., suppresses, retards, prevents, stops, delays, or reverses cancer cell infiltration into peripheral organs including, for example, the spread of cancer into soft tissue and bone; inhibit, e.g., suppress, retard, prevent, shrink, stop, delay, or reverse tumor metastasis; inhibit, e.g., suppress, retard, prevent, stop, delay, or reverse tumor growth; relieve to some extent one or more of the symptoms associated with the cancer, reduce morbidity and mortality; improve quality of life; or a combination of such effects. To the extent the drug or active agent prevents growth and/or kills existing cancer cells, it can be referred to as cytostatic and/or cytotoxic.

Terms such as "treating" or "treatment" or "to treat" or "alleviating" or "to alleviate" refer to both: 1) therapeutic measures that cure, slow down, lessen symptoms of, reverse, and/or halt progression of a diagnosed pathologic condition or disorder, and 2) prophylactic or preventative measures that prevent and/or slow the development of a targeted pathologic condition or disorder. Thus, those in need of treatment include those already with the disorder; those prone to have the disorder; and those in whom the disorder is to be prevented. A subject is successfully "treated" according to the methods disclosed herein if the subject shows one or more of the following: a reduction in the number of or complete absence of cancer cells; a reduction in the tumor size; or retardation or reversal of tumor growth, inhibition, e.g., suppression, prevention, retardation, shrinkage, delay, or reversal of metastases, e.g., of cancer cell infiltration into peripheral organs including, for example, the spread of cancer into soft tissue and bone; inhibition of, e.g., suppression of, retardation of, prevention of, shrinkage of, reversal of, delay of, or an absence of tumor metastases; inhibition of, e.g., suppression of, retardation of, prevention of, shrinkage of, reversal of, delay of, or an absence of tumor growth; relief of one or more symptoms associated with the specific cancer; reduced morbidity and mortality; improvement in quality of life; or some combination of effects. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "subject" or "individual" or "animal" or "patient" or "mammal," is meant any subject, particularly a mammalian subject, for whom diagnosis, prognosis, or therapy is desired. Mammalian subjects include, for instance, humans, domestic animals, farm animals, and zoo, sports, or pet animals such as dogs, cats, guinea pigs, rabbits, rats, mice, horses, cattle, cows, bears, and so on. The meaning of the terms "eukaryote", "animal", "mammal", and similar grammatical equivalents are well known in the art and can, for example, be deduced from Wehner and Gehring (1995; Thieme Verlag). It is also contemplated herein that the types of animals to be treated are those possessed with economic, agronomic, or scientific importance. Scientifically important organisms include, but are not limited to, mice, primates, dogs, cats, fish, nematodes, rats, and rabbits. Non-limiting examples of agronomically important animals are sheep, goats, cattle, horses, emu, alpaca, chickens, ducks, and pigs, while, for example, cats and dogs may be considered as economically important animals. In one embodiment, the subject is a mammal; in another embodiment, the subject is a human or a non-human mammal, such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig. In another embodiment, the subject is human.

II. Colchicine

In the following, colchicine used according to the embodiments described herein possess the following chemical structure (ChemID 2012):

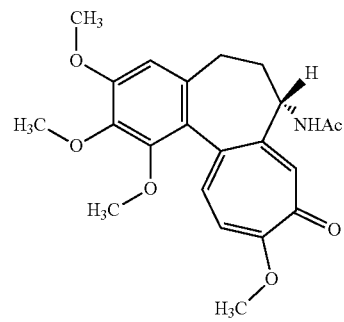 [SMILES: COc1cc2c(c(OC)c1OC)-c1ccc(OC)c(=O)cc1[C@@H](NC(C)=O)CC2]

The recognized and accepted IUPAC chemical name of colchicine is: N[5,6,7,9-tetrahydro-1,2,3,10-tetratmethoxy 9-oxobenzo[a]heptalen-7-yl],(S)-acetamide; molecular formula: $C_{22}H_{25}NO_6$; CAS number: 64-86-8.

Colchicine is an anti-inflammatory drug with a long history in human medicine, used for the symptomatic treatment of inflammatory diseases, most prominently gout. It is a natural product which can be extracted from two plants of the lily family, *Colchicum autumnale* and *Gloriosa superba*. Colchicine is a heterotricyclic alkaloid and has a molecular mass of 399.437 g/mol. The active ingredient colchicine as well as its tablet formulation is listed in various national and international pharmacopeias such as the United States Pharmacopeia (USP).

The positive effect of its plant source in the treatment of rheumatism and swelling was described first already around 1500 B.C. in Egypt. Its use in gout was first described around 1500 years ago (Graham and Roberts, 1953, *Ann. Rheum. Dis.* 12(1):16-9). Today, the therapeutic value of colchicine is well established in a number of inflammatory diseases and approved by U.S. Food and Drug Administration (FDA) for the prophylaxis and treatment of acute gout flares and FMF. Other important and established, though off-label, uses of colchicine are, Behçet's disease and recurrent pericarditis. In all known indications, colchicine is generally administered orally as solid tablets in strengths of 0.5-0.6 mg/tablet, e.g. Europe and United States, respectively. The pharmacotherapeutic mechanism of action of colchicine in diverse disorders is not fully understood, though it is known that the drug accumulates preferentially in leucocytes, particularly neutrophils, which is believed to be important for the therapeutic effect of colchicine. Three major interactions of colchicine with specific proteins are believed to modulate its pharmacokinetics: tubulin, cytochrome P450 3A4 (CYP3A4), and P-glycoprotein. It is assumed that most therapeutic effects of colchicine are related to its capacity to bind to β-tubulin, thus inhibiting self-assembly and polymerization of microtubules. Availability of tubulin is essential for several cellular functions such as mitosis. Therefore, colchicine effectively functions as a "mitotic poison" or spindle poison. By inhibiting microtubule self-assembly, colchicine interferes with many cellular functions involved in the immune response such as modulation of the production of chemokines and prostanoids and inhibition of neutrophil and endothelial cell adhesion molecules. Eventually colchicine decreases neutrophil degranulation, chemotaxis, and phagocytosis, thus reducing the initiation and amplification of inflammation. Colchicine also inhibits uric acid crystal deposition (a process important to the genesis of gout), which is enhanced by a low pH in the tissues, probably by inhibiting oxidation of glucose and subsequent lactic acid reduction in leukocytes (Imazio et al., Eur. Heart J., 30(5):532-9, 2009; Chu et al., Eur. J. Intern. Med., 21(6):503-8, 2010; Stanton et al., Med. Res. Rev., 31(3):443-81, 2011). In the management of pericarditis, colchicine is believed to exerts its therapeutic effect by suppressing acute pericardial inflammation. However, the exact cellular and molecular mechanisms of how colchicine relieves pain and inflammation in acute pericarditis and prevents recurrences are not fully understood.

Colchicine, in the context of the present disclosure can be used for inhibiting, delaying, or reducing tumor growth, or tumor metastases, or tumor growth and tumor metastases, in a subject diagnosed with, and/or suffering from, cancer.

III. Sustained Release Formulations

Disclosed are embodiments that provide a sustained release colchicine formulation to inhibit, delay, or reduce tumor growth or metastases in a subject in need thereof, e.g., a subject diagnosed with and/or suffering from cancer, wherein colchicine is released from the formulation at a sustained rate along a pre-determined or desired release profile. Such release rate is achieved by incorporation into the formulation an extended release component and an optional immediate release component. In some embodiments, the colchicine formulation described herein is formulated in a dosage form selected from a tablet, a pill, a capsule, a caplet, a troche, a sachet, a cachet, a pouch, sprinkles, or any other form suitable for oral administration.

In one embodiment, colchicine as described herein, i.e., inter alia, in the form of a (pharmaceutical) composition, is administered in the form of a sustained release preparation. Other expressions like "extended release," "controlled release," "modified release," "delayed release," "preparation," or "formulation," are understood herein to have the same meaning as "sustained release preparation." Such preparations can in principal be in any form conceivable to the skilled person and include, but are not limited to, pharmaceutical forms for oral (solid, semi-solid, liquid), dermal (dermal patch), sublingual, parenteral (injection), ophthalmic (eye drops, gel or ointment) or rectal (suppository) administration, as long as a sustained release is ensured.

In accordance with embodiments described herein, sustained release preparations encompass all pharmaceutical forms that create a steady drug release profile making the drug substance available over an extended period of time following application to the subject. In some embodiments, such an extended period of time is between 10, 20, 30, 40, 50, or 60 minutes and about 2, 3, 4, 5, 6, 7, 8, 9, 10, 11, 12, 13, 14, 15, 16, 17, 18, 19, 20, 21, 22, 23, or 24 hours. In other embodiments described herein, extended release is defined functionally as the release of over 50, 55, 60, 65, 70, 75, 80, 85, 90, 95, or 99 percent (%) of colchicine after about 10, 20, 30, 40, 50, or 60 minutes and about 2, 3, 4, 5, 6, 7, 8, 9, 10, 11, 12, 13, 14, 15, 16, 17, 18, 19, 20, 21, 22, 23, or 24 hours. The phrase, "extended release," as used herein is also defined as making colchicine available to the subject regardless of uptake, as some colchicine may never be absorbed by the subject. Various extended release dosage forms are designed readily by one of skill in art as disclosed herein to achieve delivery and sustained release of colchicine to the liver and/or both the small and large intestines, to only the small intestine, or to only the large intestine.

In some embodiments, sustained release preparations are pH independent. This allows such preparations to efficiently dissolve in almost any environment. In other embodiments, sustained release preparations are pH dependent. This allows release to be accomplished at some generally predictable or targeted location in the lower intestinal tract more distal to that which would have been accomplished if there had been no delayed release alterations. One method for achieving delayed of release of active agent in vivo is, e.g., the application of one or more coatings to the surface of the active agent, if the active agent is in the form of a pill, gel capsule, capsule, or tablet, and the like. In one embodiment, coatings applied to the dosage form are applied to a sufficient thickness such that the entire coating does not dissolve in the gastrointestinal fluids at pH below about 5, but does dissolve at pH about 5 and above. Any known anionic polymer exhibiting a pH-dependent solubility profile can be used, and is contemplated herein for use, as an enteric coating as described herein to achieve delivery of the active agent(s) to the lower gastrointestinal tract. Polymers and compatible mixtures thereof are used to provide the coating for the delayed or the extended release of active ingredients, and some of their properties include, but are not limited to, shellac, also called purified lac, a refined product obtained from the resinous secretion of an insect. This coating dissolves in media of pH>7.

In some embodiments, sustained release preparations are influenced by the presence of alcohol in the body. The presence of alcohol in a subject's body can or will alter the dissolution profile of the composition, for instance by increasing dissolution of the composition, and in some instances will lead to immediate release of the entire dose. This effect is known as "dose dumping" and is dependent on the alcohol solubility of the materials incorporated into the composition with the active agent. For sustained release preparations which contain a higher dose for slow release over 24 hours, for instance, this effect can have safety concerns and can even be life threatening.

In some embodiments, to achieve a uniform or continuous rate of release, sustained release preparations are prepared using time release hydrophilic matrices. These time release hydrophilic matrices are known in the field of drug formulations. For example, one such hydrophilic matrix is hydroxypropyl methylcellulose (HPMC, or commonly referred to as hypromellose). Hydrophilic matrices provide an initial release of the drug product in the initial phase mainly triggered by a rapid swelling of the surface of the matrix tablet, combined with an erosion process leading to an immediate release of the drug substance distributed close to the surface of the tablet. In an embodiment, about 50%, about 45%, about 40%, about 35%, about 30%, about 25%, about 20%, about 15%, or about 10% of the drug substance is immediately released depending on the desired release profile. In another embodiment, at least about 20% of the drug substance is immediately released. In another embodiment, at least about 20% of the drug substance is released within about the first 30 minutes. As used herein, the term "about" or "approximately" refers to a variation of 10% from the indicated values, e.g., 50%, 45%, 40%, etc., or in case of a range of values, means a 10% variation from both the lower and upper limits of such ranges. For instance, "about 50%" refers to a range of between 45% and 55%. Within the initial swelling of the tablet surface a gel formation of the hydrophilic matrix starts. This gelling prevents the tablet core from dissolving and disintegrating immediately, thereby allowing the main part of the drug substances to dissolve slowly over time within in this gel structure and diffuse into solution following the rules of Fick's law. The diffusion itself may be triggered in this formulation approach by the concentration of the HPMC, for example, and the viscosity of the formed gel, defined over the molecular weight of the HPMC. Therefore, drug release profiles can be modified by varying different viscosity grades of HPMC or mixtures thereof. All corresponding formulation and process parameters achieving the predicted release profile are common knowledge and can be adjusted using actual development technologies e.g. formulation screenings, statistical trials designs.

In an embodiment, the substance responsible for sustained release of the controlled-release formulation is further mixed with a binder. The binder is added to increase the mechanical strength of the granules and tablets during formation or tableting. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the formulation is in the form of a dry powder binder. Non-limiting examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include, but are not limited to, modified starch, gelatin, polyvinylpyrrolidone, cellulose derivatives (such as for example HPMC and hydroxypropyl cellulose (HPC)), polyvinyl alcohol and mixtures thereof. In an embodiment, the binder is HPMC. In another embodiment, the binder is HPMC 6 mPa·s. In another embodiment, the binder is present in an amount of from about 1% to about 30% by weight of the formulation.

In another embodiment, the sustained release formulation includes a disintegrant. A disintegrant refers to an agent used in pharmaceutical preparation of tablets that causes them to disintegrate and release their medicinal substances on contact with moisture. In an embodiment, the disintegrant is water soluble to support the disintegrantation of a tablet in the stomach. Non-limiting examples of disintegrants for use in the formulation include sucrose, lactose, in particular lactose monohydrate, trehalose, maltose, mannitol and sorbitol, croscarmellose sodium, crospovidone, alginic acid, sodium alginate, methacrylic acid divinyl benzene (DVB), cross-linked polyvinyl pyrrolidone (PVP), microcrystalline cellulose, polacrilin potassium, sodium starch glycolate, starch, pregelatinized starch, and mixtures thereof. In at least one embodiment the disintegrant is one or more of microcrystalline cellulose, e.g. Avicel PH101, cross-linked polyvinylpyrrolidone, e.g. KOLLIDON® CL, cross-linked sodium carboxymethylcellulose, e.g. AC-DI-SOL™, starch or starch derivatives, such as sodium starch glycolate, e.g. EXPLOTAB®, or combinations with starch, e.g. PRIMOJEL™, swellable ion-exchange resins, such as AMBERLITE™ IRP 88, formaldehyde-casein, e.g. ESMA SPRENG™, and mixtures thereof.

In an embodiment, lactose monohydrate is included as a filling agent in an amount of about 10% to about 80%, or about 59%, by weight of the tablet. In an embodiment, pregelatinized starch is included as a filling agent in an amount of about 5% to about 50%, or about 7.5%, by weight of the tablet.

In another embodiment, the sustained release formulation includes a release retarding agent for maintaining a uniform release rate of the drug. Examples of retarding agents include, but are not limited to, cellulose ethers, cellulose esters, acrylic acid copolymers, waxes, gums, glyceryl fatty acid esters and sucrose fatty acid esters. In one embodiment, the retarding agent is RETALAC® (Meggle), a spray agglomerated blend of 50 parts lactose monohydrate and 50 parts HPMC. The viscosity of HPMC used herein may range from 6 mPa·s to 100,000 mPa·s. In one embodiment, the viscosity of HPMC used is 4000 mPa·s. Adjusting the amount of retarding agent in the composition can under certain circumstances alter the release rate of the drug. In one embodiment, the retarding agent of the formulations or compositions described herein releases colchicine in a continuous and uniform manner and is adjusted in such a way that about 80% of the active ingredient is released in vitro in the predetermined period of time. By way of example, and by no means limiting the scope of the described compositions or formulations, the period of time is not more than 24 hours, not more than 16 hours, not more than 12 hours, not more than 8 hours, not more than 6 hours, not more than 4 hours, not more than 3.5 hours, or not more than 1.5 hours depending on desired attributes of the final product. It is understood that the release rate can vary based on whether the experiment is conducted in vitro or in vivo. Therefore, if the desired release rate is between about 1.5 to about 3.5 hours in vitro or between about 1.5 to about 6 hours in vitro, the release rate under in vivo conditions, depending on the experimental conditions, may actually be different. In an embodiment, the sustained release formulation described herein releases colchicine in a continuous and uniform manner in such a way that about 80% of the active ingredient is released in vitro in between about 1.5 and about 3.5 hours.

In another embodiment, the sustained release formulation includes a glidant. A glidant can be used to improve powder flow properties prior to and during tableting and to reduce caking. Suitable glidants include, but are not limited to, colloidal silicon dioxide, magnesium trisilicate, powdered cellulose, talc, tribasic calcium phosphate, and the like. In one embodiment, talc is included as a glidant in an amount of about 0.05% to about 5%, or about 1%, by weight of the tablet.

In another embodiment, the sustained release formulation includes a lubricant. Lubricants can be added to pharmaceutical formulations to decrease any friction that occurs between the solid and the die wall during tablet manufacturing. High friction during tableting can cause a series of problems, including inadequate tablet quality (capping or even fragmentation of tablets during ejection, and vertical scratches on tablet edges) and may even stop production.

Accordingly, lubricants are added to certain tablet formulations described herein. Non-limiting examples of lubricants useful for the core include glyceryl behenate, stearic acid, hydrogenated vegetable oils, such as hydrogenated cottonseed oil (STEROTEX®), hydrogenated soybean oil (STEROTEX® HM) and hydrogenated soybean oil & castor wax (STEROTEX® K), stearyl alcohol, leucine, polyethylene glycol (MW 1450, suitably 4000, and higher), magnesium stearate, glyceryl monostearate, polyethylene glycol, ethylene oxide polymers (for example, available under the registered trademark CARBOWAX® from Union Carbide, Inc., Danbury, Conn., US), sodium lauryl sulfate, magnesium lauryl sulfate, sodium oleate, sodium stearyl fumarate, DL-leucine, colloidal silica, mixtures thereof and others as known in the art. In one embodiment, stearic acid is included as a lubricant in an amount of about 0.05% to about 5%, or about 1%, by weight of the tablet.

In another embodiment, sweeteners are used in the taste-masking coating of certain embodiments of the matrix dosage forms, including, for example, glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; *Stevia rebaudiana* (Stevioside); chloro derivatives or sucrose such as sucralose; and sugar alcohols such as sorbitol, mannitol, xylitol, and the like. Also contemplated sweeteners include hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The controlled-release formulations described herein, in certain embodiments, further contain one or more pharmaceutically acceptable excipients such as granulating aids or agents, colorants, flavorants, pH adjusters, anti-adherents, glidants, and like excipients, conventionally used in pharmaceutical compositions. In an embodiment, a coloring excipient are advantageously added as giving rise to visual change preventing abuse or mistakes in administration. Such coloring agents can color simultaneously the liquid or the particles or either one independently of the other. Among suitable coloring excipients the following are exemplary: indigotine, cochineal carminic acid, yellow orange S, allura red AC, iron oxides, cucurmin, riboflavin, tartrazine, quinoline yellow, azorubine, amaranth, carmines, erythosine, red 2G, patented blue V, glittering blue FCF, chlorophylls, copper complexes of chlorophylls, green S, caramel, glittering black BN, carbo medicinalis vegetabilis, brown FK and HT, carotenoids, Annatto extracts, paprika extracts, lycopene, lutein, canthaxanthin, beetroot red, anthocyanes, calcium carbonate, titanium dioxide, aluminum, silver, gold or litholrubin BK or any other coloring excipient suitable for an oral administration.

In an embodiment, a sustained release formulation is coated. Coatings provide a variety of functions. In some embodiments, coatings are used, for example, to achieve delayed release, resistance to acid, targeted release in the lower gastrointestinal (GI) tract, avoidance of bad taste in mouth. In some embodiments, coatings may be used to protect the active pharmaceutical ingredient (API)/tablet from light and provide for better mechanical resistance. Of course, it is appreciated by one of skill in the art that a coating serves other functions as well depending on the circumstance and a person skilled in the art knows the purpose of tablet coating.

In one embodiment, the pharmaceutical composition and/or the solid carrier particles are coated with one or more enteric coatings, seal coatings, film coatings, barrier coatings, compress coatings, fast disintegrating coatings, or enzyme degradable coatings. In one embodiment, multiple coatings are applied for desired performance. Further, in some embodiments, one or more of the active agents incorporated into the formulations described herein are provided for immediate release, pulsatile release, controlled release, extended release, delayed release, targeted release, synchronized release, or targeted delayed release. In fact, in one embodiment, the formulation includes combinations of typical pharmaceutical actives, e.g., pseudephedrin, and vitamins, e.g., vitamin C, minerals, such as Ca, Mg, Zn, and K, for example, or other supplements, e.g., St. John's Wort, echinacea, amino acids, and the like. For release/absorption control, solid carriers are in some embodiments made of various component types and levels or thicknesses of coats, with or without an active ingredient. Such diverse solid carriers are in some embodiments blended in a dosage form to achieve a desired performance. The liquid formulations in some embodiments are delivered to, and adapted for, oral, nasal, buccal, ocular, urethral, transmucosal, vaginal, topical, or rectal delivery, although oral delivery is most common.

When formulated with microparticles or nanoparticles, the drug release profile can easily be adapted by adding a coating, e.g., a hard or soft gelatin coating, a starch coating, a resin or polymer coating and/or a cellulosic coating. Although not limited to microparticles or nanoparticles (as in, e.g., microcapsules or nanocapsules), such dosage forms are in some embodiments further coated with, for example, a seal coating, an enteric coating, an extended release coating, or a targeted delayed release coating. The term "enteric coating" as used herein relates to a mixture of pharmaceutically acceptable excipients that is applied to, combined with, mixed with or otherwise added to the carrier or composition. In one embodiment, the coating is applied to an active pharmaceutical agent that is compressed, molded, or extruded and optionally includes one or more of: gelatin, pellets, beads, granules, or particles of the carrier and/or composition. The coating is in some embodiments applied through an aqueous dispersion or after dissolving in appropriate solvent. The carrier may or may not be fully or partially biodegradable.

In an embodiment, polymethacrylate acrylic polymers are employed as coating polymers. In at least one embodiment, the coating is an acrylic resin lacquer used in the form of an aqueous dispersion, such as products commercially available from Rohm Pharma under the trade name EUDRAGIT® or from BASF under the trade name KOLLICOAT®. In other embodiments, EUDRAGIT® E100 is used as the coating polymer, which is a cationic copolymer based on dimethylaminoethyl methacrylate and neutral methacrylic esters having a average molecular weight is approximately 150,000 g/mol. Different coating polymers of the embodiments described herein are in some instances mixed together in a desired ratio to ultimately obtain a coating having a desirable drug dissolution profile. Coating methods include, for instance, spraying a solution of the polymer on the tablets, either in a pan coater or a fluid bed coating apparatus. The solvent is organic or aqueous, depending on the nature of the polymer used. In one embodiment, the solvent is alcohol. Coating methods are well known in the art.

The compositions or formulations described herein are in some embodiments formulated as enteric coated delayed release oral dosage forms, i.e., as an oral dosage form of a pharmaceutical composition as described herein that uses an enteric coating to effect release in the lower gastrointestinal tract. The enteric coated dosage form will generally include microparticles, microgranules, micropellets or microbeads of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Carriers for use with the described compositions and formulations include permeable and semipermeable matrices or polymers that control the release characteristics of the formulation. Such polymers include, for example, cellulose acylates, acetates, and other semi-permeable polymers such as those described in U.S. Pat. No. 4,285,987 (hereby incorporated by reference), as well as the selectively permeable polymers formed by the coprecipitation of a polycation and a polyanionic as disclosed in U.S. Pat. Nos. 3,173,876; 3,276,586; 3,541,005; 3,541,006 and 3,546,142 (relevant portions incorporated herein by reference).

Other carriers for use with the described compositions and formulations include, e.g., starch, modified starch, and starch derivatives, gums, including but not limited to xanthan gum, alginic acid, other alginates, bentonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan (and derivatives), gum karaya, biosynthetic gum, etc. Other useful polymers include: polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly (urethane), cross-linked chain-extended poly(urethane), poly(imides), poly(benzimidazoles), collodion, regenerated proteins, semi-solid cross-linked poly(vinylpyrrolidone).

Additional additives and their levels, and selection of a primary coating material or materials, will depend on the following properties: pH levels at target site, desirability to make tablet pH dependent or pH independent, solubility in alcohol, resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Further to the above, various formulations, not limiting the scope of the present invention, illustrating the described compositions and formulations are described hereafter. A controlled-release tablet or capsule or the like comprises colchicine as a core coated with an immediate release layer. A controlled-release double layer tablet or capsule or the like comprises a layer of sustained release and a layer of immediate release. A controlled-release tablet with more than two layers comprises: (i) one or two more layers of substance controlling the sustained release, and (ii) one or two more layers of immediate release.

According to one embodiment, the composition comprising colchicine is further coated with at least one release-slowing intermediate layer of slightly soluble intermediate layer to control release of colchicine.

Traditionally, colchicine immediate release dosage forms (mostly tablets, also injections, or oral solutions) have been used in the treatment of gout or FMF. Worldwide, all approved pharmaceuticals containing colchicine are approved only for gout and/or FMF and are immediate release tablets. Colchicine can be used in the prevention of certain other inflammatory diseases such as pericarditis, PPS and, most recently, subjects with stable coronary heart diseases. The difference between treatment and prevention with regard to colchicine is that in treatment, an overt disease and/or ongoing inflammation has to be treated. Thus, high levels of colchicine are required, which usually goes hand in hand with unwanted side effects, most prominently gastrointestinal insults, as well as increased risk of colchicine related toxicity. In prevention, one does not have to suppress ongoing inflammation but rather suppress an outbreak of inflammation. Thus, supposedly lower and steadier levels of colchicine are required and are beneficial. As described herein, this is achieved by administering colchicine formulated as a sustained release preparation, as described above.

In the case of inhibiting, delaying, or reducing tumor growth or metastases in a subject in need thereof, e.g., a cancer subject, lower or higher levels of colchicine may be necessary to inhibit interleukin (IL)-1β activity. The sustained release system facilitates more steady levels of colchicine and reduces the incidence of adverse events.

An advantage of colchicine administered as sustained release is, e.g., a flattening of the serum level curve (lower but broader peak levels) which reduces the incidence of serious adverse events related to colchicine toxicity, also in case of potential drug interactions, thereby increasing compliance. Much of colchicine-related toxicity comes from the fact that one or both of the excretion pathways (liver and kidney) is reduced in its activity, either by interactions with other drugs or by a disease, e.g. kidney insufficiency. In the case of a slower and extended drug absorption (extended release), the body has also more time to excrete the colchicine from the system. In this case, it is less likely that colchicine levels reach toxic levels in case of defective excretion (due to drug interaction or disease). Another potential advantage of colchicine administered as a sustained release formulation is that plasma levels remain more evenly distributed (i.e., the variability of plasma levels, such as the differences in $C_{max}$, $T_{max}$, AUC or other pharmacokinetic parameters, among subjects is reduced), resulting in fewer "non-responders" to the treatment. In addition, administration of colchicine as sustained release is resistant to dose dumping, therefore the dissolution of the composition is not significantly influenced by alcohol.

Further, sustaining the release expands the time where colchicine is present in the blood in therapeutic levels. This results in a more efficient inhibition of disease progression and, thus, improving the clinical outcome.

Furthermore, for the prophylactic uses described herein, colchicine does not have to go deep into the tissue (like for gout), it may be active in the blood system directly (in the vessels) where it acts on the plaques and especially on inflammatory blood cells (neutrophils). This means, less total colchicine and lower serum levels can be therapeutic.

Fast and high colchicine levels, e.g., as for treating an acute gout flare can be avoided. Thus, lower levels of colchicine, e.g., about 0.1 to about 0.75 mg sustained release formulations as described above (or even less frequent doses), may be sufficient to achieve the desired clinical outcome.

In the normal situation, most colchicine is absorbed from the small intestine and most passes the liver (some is also excreted in the urine via kidney). There it is metabolized but quite a large proportion of colchicine goes through the liver un-metabolized. This means, it goes through the liver into the bile and from there it is excreted into the big intestine (colon). There it can be resorbed into the body again which leads to the characteristic second peak (accounts for about 50% of totally absorbed colchicine and is thought to be responsible for gastrointestinal problems, such as diarrhea). If colchicine is formulated as a sustained release preparation as described above, a slower release of colchicine results in a slower resorption. This results in more complete metabolism of colchicine in the liver (because it is less busy with colchicine at a time) and, thus, less recirculation of un-metabolized colchicine. This consequently reduces the incidence of gastrointestinal problems and increases compliance. Colchicine administered as sustained release in accordance with the compositions described herein may also be beneficial for other known side/adverse effects associated with colchicine treatment/administration (the skilled person is well aware of the adverse effects that may occur upon colchicine administration or colchicine treatment). Thus, administration of colchicine as sustained release, as described above, results in a safety increase and safety benefit.

IV. Methods of Preparing a Sustained Release Formulation

Additionally, contemplated herein are methods of preparing formulations of colchicine, comprising a sustained release component, and an optional immediate release component, wherein colchicine is released from the formulation at the sustained rate along the pre-determined or desired release profile.

In one embodiment, the colchicine compositions described herein are in the form of a tablet. As used herein, the term "tablet" means a compressed pharmaceutical dosage form of any shape or size. The tablets described herein are obtained from the compositions comprising colchicine and a pharmaceutically acceptable excipient. Any of the colchicine compositions described herein can be formulated, and are contemplated to be formulated, in the form of any other dosage form known in the art, specifically, any oral dosage form, for example a capsule.

Described herein are controlled release formulations for use in oral dosage forms. The formulation includes a mixture containing HPMC as a hydrophilic matrix, which is effective to provide controlled release of a pharmaceutically active ingredient.

Matrix systems are well known in the art. In a typical matrix system, the drug is homogenously dispersed in a polymer in association with conventional excipients. This admixture is typically compressed under pressure to produce a tablet. The API is released from the tablet by diffusion and erosion. Matrix systems are described in detail by: (i) Handbook of Pharmaceutical Controlled Release Technology, Ed. D. L. Wise, Marcel Dekker, Inc. New York, N.Y. (2000), and (ii) Treatise on Controlled Drug Delivery, Fundamentals, Optimization, Applications, Ed. A. Kydonieus, Marcel Dekker, Inc. New York, N.Y. (1992), the contents of both of which are hereby incorporated by reference.

When the tablet, capsule, or pill, is exposed to aqueous media, such as in the gastrointestinal tract, the tablet surface wets and the polymer begins to partially hydrate forming an outer gel layer. This outer gel layer becomes fully hydrated and begins to erode into the aqueous fluids. Water continues to permeate toward the core of the tablet permitting another gel layer to form beneath the dissolving outer gel layer. These successive concentric gel layers sustain uniform release of the API by diffusion from the gel layer and exposure through tablet erosion. In the case of the mixtures of the present invention, when included in a compressed tablet matrix, the HPMC provides a hydrophilic swellable structure capable of functioning as the gel layer. In this way, the drug release is controlled.

In accordance with one embodiment, the colchicine formulation is manufactured by either wet or dry granulation of a colchicine composition, blending the resulting granulate with excipients, and then compressing the composition into tablets.

In one embodiment, wet granulation is used to prepare wet granules comprising colchicine. A granulating liquid is used in wet granulation process. Both aqueous and non-aqueous liquids may be used as the granulating liquid. In one embodiment, the granulating liquid is an aqueous liquid, or more specifically, purified or de-ionized water. The amount of the granulating liquid used may depend on many factors, for example, the type of the granulating liquid, the amount of the granulating liquid used, the type of excipient used, the nature of the active agent, and the active agent loading.

In one embodiment, the colchicine particles and suitable excipients are mixed with the granulating liquid for a sufficiently long period to facilitate good distribution of all starting materials and good content uniformity. Wet granulation is generally performed at temperatures between about 20° C. to about 35° C., or more specifically, at room temperature (about 25° C.). Following wet granulation, the granulate is dried at increased temperatures to yield a dry granulate. In an embodiment, the step of drying is performed for a sufficiently long period until the desired residual moisture content is reached. In an embodiment, this may be about 45° C. for about 12 to 48 hours. It should be appreciated that the overall time to perform the granulation process depends on a variety of factors, including but not limited to, the solvents used, batch size, instruments used, etc.

Any equipment used to contact the granulating liquid with the colchicine and the excipients is possible as long as uniform distribution of the granulating liquid is achieved. For example, in one embodiment, small-scale production is achieved by mixing and wetting the colchicine and the excipients in mortars or stainless steel bowls, while for larger quantities, V-blenders with intensifier bars, planetary mixers, rotary granulators, high shear granulators, and fluid-bed granulation equipment are used. In one embodiment, the granulator is a high shear granulator.

In one embodiment, a method of making a colchicine composition comprises wet granulating colchicine with pharmaceutically acceptable excipients and a granulating liquid to obtain wet granules, and mixing the granules in a next step with a second excipient to obtain a colchicine composition. In one embodiment, the pharmaceutically acceptable excipient comprises a binder and a filler. In an embodiment, the binder is HPMC. In an embodiment, the filler is lactose monohydrate and pregelatinized starch. In another embodiment, purified water is used as the granulating liquid. In an embodiment, the second excipient mixed with the granules is a filler. In an embodiment, the filler is lactose monohydrate. The colchicine compositions in some embodiments contain about 0.1 wt % to about 10 wt %, or more specifically, about 0.25 wt % to about 0.75 wt %, of colchicine, based on the total weight of the colchicine composition.

In an embodiment, the method of making a composition comprises wet granulating colchicine with a pharmaceutically acceptable excipient to obtain wet granules, and mixing the granules with a filler to obtain a colchicine composition. In some embodiments, the method further includes drying the mixture. In another embodiment, the wet granules are dried to obtain dried granules, and then the dried granules are mixed with a binder, a filler, or both to obtain the composition. In another embodiment, the dried granules are milled to obtain milled granules before mixing the milled dried granules with the binder, a filler, or both. The method further includes mixing the colchicine composition with a glidant, a lubricant, or both to obtain a blend or compressing the blend to obtain a tablet, in certain embodiments. In one embodiment, the glidant is talc. In another embodiment, the lubricant is stearic acid. The method further includes coating the tablet in certain embodiments.

In another embodiment, a method of making a colchicine tablet comprises wet granulating colchicine with a pharmaceutically acceptable excipient to obtain wet granules; drying the wet granules to obtain dried granules; milling the dried granules to obtain milled granules; mixing the milled granules with a filler to obtain the composition; mixing the composition with a glidant, a lubricant, or both to obtain a blend; and compressing the blend to obtain a colchicine tablet as described herein.

In some embodiments, the wet granules are dried to obtain dried granules before mixing with a second excipient, for example a filler. Wet granules are dried by any known suitable processes to remove the granulating liquid and to form dried granules containing colchicine and the pharmaceutically acceptable excipient. The conditions and duration of drying depend on factors such as the liquid used and the weight of the granulating particles. Examples of suitable drying methods include, but are not limited to, tray drying, forced air drying, microwave drying, vacuum drying and fluid bed drying.

After drying, dried granules may be mixed directly with an excipient, for example, a filler, a binder, or a lubricant, for further processing. Alternatively, dried granules may optionally be subjected to additional processing steps prior to mixing with the excipient. For example, dried granules may be sized to reduce particle size prior to mixing with an excipient. Exemplary sizing operations include milling or sieving. Any suitable equipment for reducing the particle size can be used.

Suitable excipients are added extragranularly in some embodiments, and mixed with the granules to form colchicine compositions. As used herein, the term "extragranular" or "extragranularly" as used herein means that the referenced material, for example, a suitable excipient, is added or has been added as a dry component after wet granulation. In one embodiment, a filler, a binder, a glidant, and/or a lubricant are added extragranularly to the granules and mixed to form a blend. The blend is in some embodiments encapsulated directly into capsule shells, for example, hard gelatin shells, to form capsule formulations. Alternatively, the blend is in some embodiments compressed into tablets. In some embodiments, the granules are dried granules or milled, dried granules.

Mixing is performed for a sufficient time to produce homogeneous mixtures or blends. Mixing is accomplished by blending, stirring, shaking, tumbling, rolling, or by any other method to achieve a homogeneous blend. In some embodiments, the components to be mixed are combined under low shear conditions in a suitable apparatus, such as a V-blender, tote blender, double cone blender, or any other similar apparatus capable of functioning under low shear conditions.

The homogenous mixtures or blends are then compressed using any method suitable in the industry. The mechanical force of compression will define the physical properties of the tablets, especially the crushing strength of the resulting tablet. The mechanical strength interacts with the initial swelling of the tablet and dilution speed of the tablet core. This effect is well known in the art and can be adjusted and controlled during the lifecycle of the product. For the colchicine sustained-release formulation described herein, the compression strengths used may range from about 30N to about 130N. In one embodiment, the compression strength may be about 100N. In another embodiment, the compression strength is about 100N+/−15N.

The colchicine tablets prepared from the above described methods exhibit acceptable physical characteristics including good friability and hardness. As per European Pharmacopoeia (EP) and USP guidelines, the colchicine tablets disclosed herein have friability in the range of about 0% to less than about 1%.

As already noted above, the colchicine tablet are coated in some embodiments. Coating the tablet is performed by any known process. A coating for the colchicine tablet disclosed herein is any suitable coating, such as, for example, a functional or a non-functional coating, or multiple functional or non-functional coatings. The phrase "functional coating" as used herein includes a coating that modifies the release properties of the total formulation, for example, a sustained-release coating. The phrase "non-functional coating" as used herein includes a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

In one embodiment, a colchicine composition comprises colchicine, a binder, a filler, a retarding agent, a glidant, and a lubricant. In an embodiment, a colchicine composition comprises about 0.25 to about 0.75 mg colchicine; about 10 to about 80 mg lactose monohydrate; about 5 to about 50 mg pregelatinized starch; about 1 to about 30 mg HPMC 6 mPa·s; about 5 to about 40 mg RETALAC® (compound of lactose monohydrate and HPMC 4000 mPa·s 50/50 w/w %); about 0.5 to about 5 mg talc; and about 0.5 to about 5 mg stearic acid. In an embodiment, the colchicine composition comprises about 0.5 mg colchicine, about 59 mg lactose monohydrate; about 7.5 mg pregelatinized starch; about 1 mg HPMC 6 mPa·s; about 30 mg RETALAC® (compound of lactose monohydrate and HPMC 4000 mPa·s 50/50 w/w %); about 1 mg talc; and about 1 mg stearic acid. The colchicine dosage form has a total weight of about 100 mg. The colchicine composition can be in the form of a tablet.

V. Treatment Methods Using Sustained Release Colchicine as a Single Agent or in Combination with at Least One Immune Modulating Therapy Also described herein are methods to inhibit, delay, or reduce tumor growth, or tumor metastases, in a subject in need thereof, e.g., a cancer subject, comprising administering to the subject a therapeutically effective amount of a colchicine formulation as described herein, wherein colchicine is released from the formulation at a sustained rate along a pre-determined or desired release profile. The methods described herein possesses the flexibility to selectively adjust the pharmacokinetics of the administered formulations depending on the nature of the condition and needs of the subjects due to the specifically tailored design of the colchicine formulation described herein that comprises an extended release component and an optional immediate release component, and the release profiles of both components can be selectively modified during the preparation process as described above to comply with the predetermined release profile.

In one embodiment, treatment includes the application or administration of a colchicine formulation as described herein to a subject, where the subject has, or has the risk of developing cancer. In another embodiment, treatment is also intended to include the application or administration of a pharmaceutical composition comprising the colchicine formulation, to a subject, where the subject has, or has the risk of developing cancer.

Colchicine is an anti-inflammatory agent, known as the drug of choice for management of gout. It has been shown that the anti-inflammatory effect of colchicine is mediated by inhibition of the release of pro-inflammatory cytokines IL-1 and IL-1β. Moreover, by restrain of the NF-κB pathway and blocking cell mitosis, colchicine may exert an inhibitory effect on tumorigenesis. Addition of colchicine to human lipopolysaccharide (LPS) stimulated peripheral blood mononuclear cells (PBMC) exerted a disruptive effect on cellular microtubules with a consequent increased IL-1β and a decreased TNF-α release. In a recent study it has been shown that colchicine added to co-cultures of PBMC with either HT-29 or RKO human colon cancer cells promoted cancer cells-stimulated PBMC to produce IL-1β and to inhibit the release of tumor necrosis factor (TNF)-α and IL-10. It is conceivable that colchicine may act on tumor development by modulation of the immune balance between immune and cancer cells with a subsequent interference in production of inflammatory cytokines by cancer cell-activated PBMC. A similar tumor cell-macrophage cross-talk has been observed in other studies. TNF-α released from colon cancer cells stimulated TNF-α and colony stimulating factor (CSF)-1 production by mouse macrophages indicating the existence of an immune intercellular communication between these cell types. Furthermore, it has been shown that monocytes interacting with cancer cells differentiate into tumor-associated macrophages that may be associated with angiogenesis and metastasis.

On an indication and subject-by-subject basis, not all tumors contain immune cells. Tumor types that on average harbor a greater concentration of infiltrating leukocytes include: melanoma, colorectal cancer, non-small cell lung cancer, and head and neck squamous cell carcinoma. In these tumors the lymphocytic infiltrate is thought to reflect how foreign or "visible" a tumor is to the immune system which in turn is connected to the extent of "disregulation" or "aberration" within the tumor. Yet despite effective recruitment of immune cells to the tumor, they generally do not succumb to immune-mediated regression. This is believed to be the effect of suppressive or resistance mechanisms adopted by the tumor. These mechanisms generally include the activity of myeloid derived suppressor cells (MDSC), M2 macrophage, regulatory T cells, and dendritic cells on defective antigen presentation, the production of suppressive cytokines, impaired costimulation for effector T cells and antigen loss.

In tumors with high numbers of infiltrating leukocytes, a new class of therapeutics called checkpoint inhibitors has been shown to release or remove suppressive immune elements including regulatory T cells. The leading class of these molecules target the proteins PD1, PDL1 or CTLA4 although there are others approved and still many others in various stages of clinical approval across the range of suppressive mechanisms.

"Disregulation" in tumors with high lymphocytic content is highly correlated with the total number of genetic mutations that tumor harbors which in turn translates to the production of defective and novel (foreign) proteins which serve as antigens that prime the immune response. In a very simplistic sense: high tumor burden→tumor formation→increased antigenicity→increased lymphocytic infiltrate→induction of resistance marked by the production of suppressive cytokines such as IL-10.

Given the anti-inflammatory effect of colchicine, colchicine is likely most effective in the scenario described above including reduction of IL-10 as has been published.

Identifying tumors with high lymphocytic burden can be difficult in the absence of biopsy. However, subjects with Lynch Syndrome (also known as hereditary non-polyposis colorectal cancer) are known to harbor germline mutations in critical mismatch repair genes that predispose them to tumors with high mutational burden. Specifically, Lynch Syndrome is known to effect 1 in 400 persons and elevate their lifetime risk of developing the following cancers: colorectal cancer—lifetime disease probability of 70%, mean age of onset of 44-61; gastric cancer—lifetime disease probability of 10%, mean age of onset of 56; endometrial cancer—lifetime disease probability of 40%, mean age of onset of 48-62; ovarian cancer—lifetime disease probability of 10%, mean age of onset of 42.

Indeed, one diagnostic for Lynch Syndrome in subjects includes genetic testing for a phenomenon called microsatellite instability (or MSI+) characterized by slippage of small tandem repeat elements within the genome indicative of wide-spread, excessive mutational burden. Approximately 95% of Lynch Syndrome tumors are MSI+. In May of 2017, the FDA approved the use of Pembrolizumab for MSI+ subject tumors representing the first such approval based on a biomarker rather than an indication. In other words, Pembrolizumab is approved for use for any MSI+ tumor.

Lynch Syndrome subjects may be diagnosed at the time of treatment or as part of familial genetic screens. Therefore, the opportunity exists to treat subjects either acutely to assess the ability of colchicine to augmenting checkpoint inhibitors such as Ipilimumab, Pembrolizumab and Nivolumab or prophylactically where it would be used as a single agent at a non-toxic dose known to suppress inflammation.

Alternatively, without wishing to be bound by any specific teleology or theory on the biological mechanism, colchicine may exert its anti-tumor activity by its inhibitory effect on IL-1b mediated activity. A recent study has shown significantly reduced tumor incidence and mortality in subjects treated with a selective IL-1b inhibiting monoclonal antibody. The effect was especially pronounced in lung cancers incidence. This study indicates that inhibition of IL-1b signaling (in tumor cells, immune cells or non-immune cells) may be protective at least in certain tumors and in certain tumor stages.

Alternatively, and again without intending to be bound by any specific theory, some of the anti-tumor activity of colchicine may stem from direct effects of colchicine contacting tumor cells. It is known that colchicine is internalized especially by fast-growing cells. Colchicine may inhibit cell division of tumor cells by inhibition of micro-tubule function.

Therefore, colchicine is contemplated to be used herein to inhibit, delay, or reduce tumor growth or metastases in a subject in need of such inhibition, delay, or reduction, e.g., a cancer subject. Cancers include, but are not limited to, carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, and a combination thereof. Especially, in the context of the present disclosure, colchicine is used to inhibit, delay, or reduce tumor growth or metastases in a subject having lung cancer.

In accordance with the present disclosure, the colchicine formulation described herein is used to promote a positive therapeutic response with respect to tumor growth and/or metastases. The phrase "positive therapeutic response" as used herein, with respect to cancer treatment, is intended an improvement in the disease in association with the anti-tumor activity of these binding molecules, e.g., antibodies or fragments thereof, and/or an improvement in the symptoms associated with the disease. In particular, the methods provided herein are directed to inhibiting, preventing, reducing, alleviating, delaying, or lessening growth of a tumor and/or the development of metastases of primary tumors in a subject. That is, the prevention of distal tumor outgrowths can be observed. Thus, for example, an improvement in the disease may be characterized as a complete response. As used herein, the phrase "complete response" is intended an absence of clinically detectable metastases with normalization of any previously abnormal radiographic studies, e.g. at the site of the primary tumor or the presence of tumor metastases in bone marrow. Alternatively, an improvement in the disease may be categorized as being a partial response. As used herein, the phrase "partial response" is intended at least about a 50% decrease in all measurable metastases (i.e., the number of tumor cells present in the subject at a remote site from the primary tumor). Alternatively, an improvement in the disease may be categorized as being relapse free survival or "progression free survival". As used herein, the phrase "relapse free survival" is intended the time to recurrence of a tumor at any site. As used herein, the phrase "progression free survival" means the time before further growth of tumor at a site being monitored can be detected.

Inhibition, delay, or reduction of metastases is normally assessed using screening techniques such as imaging, for example, fluorescent antibody imaging, bone scan imaging, and tumor biopsy sampling including bone marrow aspiration (BMA), or immunohistochemistry. In addition to these positive therapeutic responses, the subject undergoing therapy with a colchicine molecule of the present invention, can experience the beneficial effect of an improvement in the symptoms associated with the disease.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by enzyme-linked immunosorbent assay (ELISA), radioimmunoassay (RIA), chromatography, and the like.

In another embodiment, the colchicine formulation as described herein is useful in the prevention of tumor growth and/or metastases. As used herein, the term "prevention" is well known in the art. For example, a subject suspected of being prone to suffer from a disorder or disease as defined herein may, in particular, benefit from a prevention of the disorder or disease. The subject may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the subject, for example, the subject does not show any clinical or pathological symptoms. Thus, the term "prevention" as used herein comprises the use of compounds of the present invention before any clinical and/or pathological symptoms are diagnosed or determined or can be diagnosed or determined by the attending physician. Prevention includes, without limitation, to avoid the disease or condition from occurring in subject that may be predisposed to the disease but does not yet experience or exhibit symptoms of the disease (prophylactic treatment).

Colchicine is also optionally used in combination with at least one other immune modulating therapy, as described herein, to inhibit, delay, or reduce tumor growth or metastases in a subject in need of such inhibition, delay, or reduction, e.g., a cancer subject.

In one embodiment, the immune modulating therapy includes one or more of cancer vaccines, immunostimulatory agents, adoptive T cell or antibody therapy, and inhibitors of immune checkpoint blockade (Lizée et al., *Annu. Rev. Med.*, 64:71-90, 2013).

Cancer Vaccines. Cancer vaccines activate the body's immune system and natural resistance to an abnormal cell, such as cancer, resulting in eradication or control of the disease. Cancer vaccines generally include a tumor antigen in an immunogenic formulation that activates tumor antigen-specific helper cells and/or CTLs and B cells. Vaccines can be in a variety of formulations, including, but not limited to, dendritic cells, especially autologous dendritic cells pulsed with tumor cells or tumor antigens, heterologous tumor cells transfected with an immune stimulating agent such as GM-CSF, recombinant virus, or proteins or peptides that are usually administered together with a potent immune adjuvant such as CpG.

Immunostimulatory Agents. Immunostimulatory agents act to enhance or increase the immune response to tumors, which is suppressed in many cancer subjects through various mechanisms. Immune modulating therapies may target lymphocytes, macrophages, dendritic cells, natural killer cells (NK Cell), or subsets of these cells such as cytotoxic T lymphocytes (CTL) or Natural Killer T (NKT) cells. Because of interacting immune cascades, an effect on one set of immune cells will often be amplified by spreading to other cells, e.g. enhanced antigen presenting cell activity promotes response of T and B lymphocytes. Examples of immunostimulatory agents include, but are not limited to, HER2, cytokines such as G-CSF, GM-CSF and IL-2, cell membrane fractions from bacteria, glycolipids that associate with CD1d to activate NKT cells, CpG oligonucleotides.

Macrophages, myelophagocytic cells of the immune system, are a fundamental part of the innate defense mechanisms, which can promote specific immunity by inducing T cell recruitment and activation. Despite this, their presence within the tumor microenvironment has been associated with enhanced tumor progression and shown to promote cancer cell growth and spread, angiogenesis and immunosuppression. Key players in the setting of their phenotype are the microenvironmental signals to which macrophages are exposed, which selectively tune their functions within a functional spectrum encompassing the M1 (tumor inhibiting macrophage) and M2 (tumor promoting macrophage) extremes. (Sica et al., *Seminars in Cancer Biol.*, 18:349-355, 2008). Increased macrophage numbers during cancer generally correlates with poor prognosis. (Qualls and Murray, *Curr. Topics in Develop. Biol.*, 94:309-328, 2011). Of the multiple unique stromal cell types common to solid tumors, tumor-associated macrophages (TAMs) are significant for fostering tumor progression. Targeting molecular pathways regulating TAM polarization holds great promise for anticancer therapy. (Ruffell et al., *Trends in Immunol.*, 33:119-126, 2012).

Adoptive Cell Transfer. Adoptive cell transfer employs T cell-based cytotoxic responses to attack cancer cells. Autologous T cells that have a natural or genetically engineered reactivity to a subject's cancer are generated and expanded in vitro and then transferred back into the cancer subject. One study demonstrated that adoptive transfer of in vitro expanded autologous tumor-infiltrating lymphocytes was an effective treatment for subjects with metastatic melanoma. (Rosenberg et al., *Nat. Rev. Cancer*, 8(4):299-308, 2008). This can be achieved by taking T cells that are found within resected subject tumor. These T cells are referred to as tumor-infiltrating lymphocytes (TIL) and are presumed to have trafficked to the tumor because of their specificity for tumor antigens. Such T cells can be induced to multiply in vitro using high concentrations of IL-2, anti-CD3 and alloreactive feeder cells. These T cells are then transferred back into the subject along with exogenous administration of IL-2 to further boost their anti-cancer activity. In other studies, autologous T cells have been transduced with a chimeric antigen receptor that renders them reactive to a targeted tumor antigen (Liddy et al., *Nature Med.*, 18:980-7, 2012; and Grupp et al., *New England J. Med.*, 368:1509-18, 2013).

Other adoptive cell transfer therapies employ autologous dendritic cells exposed to natural or modified tumor antigens ex vivo that are re-infused into the subject. PROVENGE® is such an FDA-approved therapy in which autologous cells are incubated with a fusion protein of prostatic acid phosphatase and GM-CSF to treat subjects with prostate tumors. GM-CSF is thought to promote the differentiation and activity of antigen presenting dendritic cells (Small et al., *J. Clin. Oncol.*, 18:3894-903, 2000; and U.S. Pat. No. 7,414, 108).

Immune Checkpoint Blockade. Immune checkpoint blockade therapies enhance T-cell immunity by removing a negative feedback control that limits ongoing immune responses. These types of therapies target inhibitory pathways in the immune system that are crucial for modulating the duration and amplitude of physiological immune responses in peripheral tissues in order to minimize collateral tissue damage. Tumors can evolve to exploit certain immune-checkpoint pathways as a major mechanism of immune resistance against T cells that are specific for tumor antigens. Since many immune checkpoints are initiated by ligand-receptor interactions, these checkpoints can be blocked by antibodies to either receptor or ligand or may be modulated by soluble recombinant forms of the ligands or receptors. Neutralization of immune checkpoints allows tumor-specific T cells to continue to function in the otherwise immunosuppressive tumor microenvironment. Examples of immune checkpoint blockade therapies are those which target Cytotoxic T-lymphocyte-associated antigen 4 (CTLA-4), PD-1, its ligand PD-L1, LAG3, and B7-H3.

Cyclophosphamide. Cyclophosphamide, a commonly used chemotherapeutic agent, can enhance immune responses. Cyclophosphamide differentially suppresses the function of regulatory T cells ($T_{regs}$) relative to effector T cells. $T_{regs}$ are important in regulating anticancer immune responses. Tumor-infiltrating $T_{regs}$ have previously been associated with poor prognosis. While agents that target $T_{regs}$ specifically are currently unavailable, cyclophosphamide has emerged as a clinically feasible agent that can preferentially suppress $T_{regs}$ relative to other T cells and, therefore, allows more effective induction of antitumor immune responses.

In another embodiment, therapy with a colchicine molecule may be combined with either low dose chemotherapy or radiation therapy. Although standard chemotherapy is often immunosuppressive, low doses of chemotherapeutic agents such as cyclophosphamide, doxorubicin, and paclitaxel have been shown to enhance responses to vaccine therapy for cancer (Machiels et al., *Cancer Res.*, 61:3689-3697, 2001). In some cases, chemotherapy may differentially inactivate T regulatory cells ($T_{regs}$) and MDSC that negatively regulate immune responses in the tumor environment. Radiation therapy has been generally employed to exploit the direct tumoricidal effect of ionizing radiation. Indeed, high dose radiation can, like chemotherapy, be immunosuppressive. Numerous observations, however, suggest that under appropriate conditions of dose fractionation and sequencing, radiation therapy can enhance tumor-specific immune responses and the effects of immune modulating agents. One of several mechanisms that contribute to this effect is cross-presentation by dendritic cells and other antigen presenting cells of tumor antigens released by radiation-induced tumor-cell death (Higgins et al., *Cancer Biol. Ther.*, 8:1440-1449, 2009). In effect, radiation therapy may induce in situ vaccination against a tumor (Ma et al., *Seminar Immunol.*, 22:113-124, 2010) and this could be amplified by combination with therapy with colchicine.

In one embodiment, the immune modulating therapy may be an immune modulating agent, including, but not limited to, interleukins such as IL-2, IL-7, IL-12; cytokines such as granulocyte-macrophage colony-stimulating factor (GM-CSF), interferons; various chemokines such as CXCL13, CCL26, CXCL7; antagonists of immune checkpoint blockades such as anti-CTLA-4, anti-PD-1, anti-PD-L1, anti-LAG3 and anti-B7-H3; synthetic cytosine phosphate-guanosine (CpG), oligodeoxynucleotides, glucans, modulators of regulatory T cells ($T_{regs}$) such as cyclophosphamide, or other immune modulating agents. In one embodiment, the immune modulating agent is an agonist antibody to 4-1BB (CD137). As recently reported, such agonist antibody to 4-1BB can give rise to a novel class of KLRG1+ T cells that are highly cytotoxic for tumors (Curran et al., *J. Exp. Med.*, 210:743-755, 2013). In all cases, the additional immune modulating therapy is administered prior to, during, or subsequent to the colchicine molecule. Where the combined therapies comprise administration of a colchicine molecule in combination with administration of another immune modulating agent, the methods of the invention encompass co-administration, using separate formulations or a single pharmaceutical formulation, with simultaneous or consecutive administration in either order.

In one embodiment, the immune modulating therapy is a cancer therapy agent, including, but not limited to, surgery or surgical procedures, e.g. splenectomy, hepatectomy, lymphadenectomy, leukophoresis, bone marrow transplantation, and the like; radiation therapy; chemotherapy, optionally in combination with autologous bone marrow transplant, or other cancer therapy; where the additional cancer therapy is administered prior to, during, or subsequent to the colchicine therapy. Where the combined therapies comprise administration of colchicine as described herein in combination with administration of another therapeutic agent, the methods described herein encompass co-administration, using separate formulations or a single pharmaceutical formulation, with simultaneous or consecutive administration in either order.

In one embodiment, treatment includes the application or administration of colchicine as described herein as a single agent or in combination with at least one other immune modulating therapy to a subject, or application or administration of colchicine as a single agent or in combination with at least one other immune modulating therapy to an isolated tissue or cell line from a subject, where the subject has, or has the risk of developing metastases of cancer cells. In another embodiment, treatment is also intended to include the application or administration of a pharmaceutical composition comprising colchicine in combination with at least one other immune modulating therapy or application or administration of a pharmaceutical composition comprising colchicine and at least one other immune modulating therapy to an isolated tissue or cell line from a subject, where the subject has, or has the risk of developing metastases of cancer cells.

Colchicine as single agents or in combination with at least one other immune modulating therapy are useful for the treatment of various malignant and non-malignant tumors. The phrase "anti-tumor activity" as used herein is intended to mean a reduction in the rate of IL-1β production or accumulation associated directly with the tumor or indirectly with stromal cells of the tumor environment, and hence a decline in growth rate of an existing tumor or of a tumor that arises during therapy, and/or destruction of existing neoplastic (tumor) cells or newly formed neoplastic cells, and hence a decrease in the overall size of a tumor and/or the number of metastatic sites during therapy. For example, therapy with colchicine as a single agent or in combination with at least one other immune modulating therapy causes a physiological response, for example, a reduction in metastases, that is beneficial with respect to treatment of disease states associated with IL-1β-expressing cells in the subject.

In one embodiment, the use of colchicine as a single agent or in combination with at least one other immune modulating therapy as a medicament is contemplated herein in the treatment or prophylaxis of cancer or for use in a precancerous condition or lesion to inhibit, reduce, prevent, delay, or minimalize the growth or metastases of tumor cells.

In accordance with the methods described herein, colchicine as a single agent or in combination with at least one other immune modulating therapy is used to promote a positive therapeutic response with respect to a malignant human cell. The phrase "positive therapeutic response" as used herein, with respect to cancer treatment, is intended to mean an improvement in the disease in association with the anti-tumor activity of these binding molecules, e.g., antibodies or fragments thereof, and/or an improvement in the symptoms associated with the disease. In particular, the methods provided herein are directed to inhibiting, preventing, reducing, alleviating, delaying, or lessening growth of a tumor and/or the development of metastases of primary tumors in a subject. That is, the prevention of distal tumor outgrowths can be observed. Thus, for example, an improvement in the disease is in some instances characterized as a complete response. The phrase "complete response" as used herein is intended to mean an absence of clinically detectable metastases with normalization of any previously abnormal radiographic studies, e.g. at the site of the primary tumor or the presence of tumor metastases in bone marrow. Alternatively, an improvement in the disease may be categorized as being a partial response. The phrase "partial response" as used herein, is intended to mean at least about a 50% decrease in all measurable metastases (i.e., the number of tumor cells present in the subject at a remote site from the primary tumor). Alternatively, an improvement in the disease may be categorized as being relapse free survival or "progression free survival". The phrase "relapse free survival" as used herein is intended to mean the time to recurrence of a tumor at any site. "Progression free survival" is the time before further growth of tumor at a site being monitored can be detected.

Inhibition, delay, or reduction of metastases can be assessed using screening techniques such as imaging, for example, fluorescent antibody imaging, bone scan imaging, and tumor biopsy sampling including bone marrow aspiration (BMA), or immunohistochemistry. In addition to these positive therapeutic responses, the subject undergoing therapy with colchicine as described herein can experience the beneficial effect of an improvement in the symptoms associated with the disease.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

In an embodiment, the use of colchicine is in fixed (within the same pharmaceutical preparation) or unfixed (different pharmaceutical preparation) combination. "Fixed combination" as used herein is to be understood as meaning a combination whose active ingredients are combined at fixed doses in the same vehicle (single formula) that delivers them together to the point of application. Fixed combination means, e.g., in a single tablet, solution, cream, capsule, gel, ointment, salve, patch, suppository or transdermal delivery system. "Unfixed combination" as used herein is to be understood as meaning that the active ingredients/components are in more than one vehicle, e.g. tablets, solutions, creams, capsules, gels, ointments, salves, patches, suppositories or transdermal delivery systems. Each of the vehicles can contain a desired pharmaceutical composition or active component.

VI. Pharmaceutical Compositions and Administration Methods

Methods of preparing and administering the colchicine formulation described herein to a subject in need thereof are well known to or are readily determined by those skilled in the art. The route of administration of the colchicine formulation is, for example, oral, parenteral, by inhalation or topical. The term "parenteral" as used herein includes, e.g., intravenous, intraarterial, intraperitoneal, intramuscular, subcutaneous, rectal, or vaginal administration. While all these forms of administration are clearly contemplated as being within the scope of the present disclosure, an example of a form for administration would be a solution for injection, in particular for intravenous or intraarterial injection or drip. A suitable pharmaceutical composition for injection can comprise a buffer, e.g., acetate, phosphate or citrate buffer, a surfactant, e.g., polysorbate, optionally a stabilizer agent, e.g., human albumin, etc. However, in other methods compatible with the teachings herein, colchicine as a single agent or in combination with at least one other immune modulating therapy can be delivered directly to the site of the adverse cellular population thereby increasing the exposure of the diseased tissue to the therapeutic agent.

Colchicine, when used as a composition in the context of the present disclosure, in some instances includes one or more pharmaceutically acceptable carriers and thus is prepared in the form of a local formulation, for the composition to be administered. The pharmaceutically acceptable carrier optionally includes saline, sterile water, linger liquid, buffer saline, a dextrose solution, a malto dextrin solution, glycerol, ethanol, and mixtures of one or more thereof, and also optionally includes an additive such as an antioxidant, a buffer, a bacteriostatic agent or the like, as necessary. Furthermore, a diluent, a dispersant, a surfactant, a binder, and a lubricant is added in some embodiments added when the composition is prepared, e.g., in the form of a local formulation such as an ointment, lotion, cream, gel, skin emulsion, skin suspension, patch, or spray.

Non-limiting examples for administration of the compound and or compositions described herein include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets. The composition according to the present invention can administered in any pharmaceutical form for oral, e.g., solid, semi-solid, liquid, dermal, e.g., dermal patch, sublingual, parenteral, e.g., injection, ophthalmic, e.g., eye drops, gel or ointment, or rectal, e.g., suppository administration. In an embodiment, the composition is formulated as a tablet, capsule, suppository, dermal patch, or sublingual formulation.

The pharmaceutical compositions described herein comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01 M to 0.1 M, or 0.05 M, phosphate buffer, or 0.8% saline. Other common parenteral vehicles include, but are not limited to, sodium phosphate solutions, Ringer's dextrose, dextrose and sodium chloride, lactated Ringer's, or fixed oils. Intravenous vehicles include, but are not limited to, fluid and nutrient replenishers, electrolyte replenishers, such as those based on Ringer's dextrose, and the like. Preservatives and other additives are also present in some embodiments, such as, for example, antimicrobials, antioxidants, chelating agents, and inert gases, and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringeability exists. Compositions or formulations described herein should be stable under the conditions of manufacture and storage and will preferably be preserved against the contaminating action of microorganisms, such as bacteria and fungi. The carrier is in some embodiments a solvent or dispersion medium containing, for example, water, ethanol, polyol, e.g., glycerol, propylene glycol, and liquid polyethylene glycol, and the like, and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co., 16th ed., 1980).

Prevention of infection by microorganisms is achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions is brought about by including in the composition an agent which delays absorption, for example, aluminum monostearate and gelatin.

In any case, sterile injectable solutions are contemplated herein and are in some instances prepared by incorporating an active compound, e.g., colchicine, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture can have labels or package inserts indicating that the associated compositions are useful for treating a subject suffering from, or predisposed to a disease or disorder.

Parenteral formulations are in some embodiments a single bolus dose, an infusion, or a loading bolus dose, followed with a maintenance dose. These compositions are in such embodiments administered at specific fixed or variable intervals, e.g., once a day, or on an "as needed" basis.

Certain pharmaceutical compositions contemplated herein are orally administered in an acceptable dosage form including, e.g., capsules, tablets, and aqueous suspensions or solutions. Certain pharmaceutical compositions also are administered by nasal aerosol or inhalation. Such compositions are prepared as solutions in saline, employing benzyl alcohol or other suitable preservatives, absorption promoters to enhance bioavailability, and/or other conventional solubilizing or dispersing agents.

The amount of the colchicine formulation to be combined with the carrier materials to produce a single dosage form will vary depending upon the host treated and the particular mode of administration. The composition is administered as a single dose, multiple doses, or over an established period of time in an infusion. Dosage regimens also are adjusted to provide the optimum desired response, e.g., a therapeutic or prophylactic response.

The compositions described herein are in some embodiments administered in a dose range varying depending on the subject's body weight, age, gender, health condition, diet, administration time, administration method, excretion rate, and disease severity. The compounds described herein as compounds per se in their use as pharmacophores or as pharmaceutical compositions are administered to the subject at a suitable dose. The dosage regimen will be determined by the attending physician based on various clinical factors. As is well known in the medical arts, dosages for any one subject depends upon many factors, including the subject's size, body surface area, age, the particular compound to be administered, sex, time, and route of administration, general health, and other concurrently administered drugs. Generally, the regimen as a regular administration of the pharmaceutical composition comprising the herein defined compositions should be, e.g., in a range as described below. Progress is then monitored by periodic assessment.

The compositions described herein are in some embodiments administered with a single dose or with 2, 3, 4, 5, 6, 7, 8, 9, or 10 doses, if desired. The composition is administered 1, 2, 3, 4, 5, 6, 7, 8, 9, or 10 times per day. In one embodiment, colchicine described herein is administered once per day. In another embodiment, colchicine is administered once per day as a single dose.

The compositions described herein are in some embodiments administered regularly for long periods of time. In an embodiment, the composition can be administered regularly for 1, 2, 3, 4, 5, 6, 7, 8, 9, 10, or more years. In another embodiment, the composition can be administered regularly for 1, 2, 3, 4, 5, 6, 7, 8, 9, 10, 11, 12, or more months. In other embodiments, the composition can be administered regularly for 1, 2, 3, 4, 5, 6, 7, 8, 9, 10, or more weeks. As used herein, the term "regularly" refers to administration of the composition at regular times or intervals over a period of time. For instance, the composition is administered in some embodiments to a subject once daily for three (3) years. In other embodiments, the composition is administered to a subject once every other day for five (5) years. It should be appreciated that the frequency of administration will vary based on a number of factors, including, but not limited to, the severity of disease, the overall health of the subject, any additional medications the subject is taking, and whether the treatment is intended to be prophylactic or not. It should also be appreciated that the frequency of administration of the disclosed compositions may be adjusted at any point during the treatment regimen.

The amount/concentration/dose of the composition according to the present invention can be between 0.1 mg and 5.0 mg, 0.1 mg and 2.0 mg, 0.1 mg to 1.5 mg, 0.1 mg to 1.0 mg, 0.1 mg to 0.75 mg, 0.1 mg to 0.5 mg, 0.25 mg to 5.0 mg, 0.25 mg to 2.0 mg, 0.25 mg to 1.5 mg, 0.25 mg to 1.0 mg, 0.25 mg to 0.75 mg or 0.25 mg to 0.5 mg. In an embodiment, the composition is administered at a daily dose of colchicine of between about 0.1 mg and about 0.75 mg or between about 0.1 mg and about 0.5 mg. In another embodiment, the composition is administered at a daily dose of colchicine of between about 0.25 mg to about 0.75 mg or between about 0.25 mg to about 0.5 mg. In an embodiment, the composition is administered at a daily dose of about 0.5 mg colchicine.

In one embodiment, the amount/concentration of colchicine as used herein is administered on the first day of administration in a higher dose (concentration/amount) compared to the administration of colchicine on the following days(s) of administration (maintenance administration/maintenance dose of administration). In other embodiments, such decreased dose (maintenance dose) is started after 2, 3, 4, 5, 6, 7, 8, 9, or 10 days of initial administration of the higher dose. In case the course of treatment is as described above, the higher dose/amount/concentration of colchicine, e.g. at the first day of administration is any as described above, provided that the maintenance dose (the dose/amount/concentration of colchicine at the days following the higher dose/amount/concentration) is lower than the initial dose/amount/concentration of colchicine, e.g. at the first day of administration. In one embodiment, the compositions described herein are administered with a dose of colchicine of between about 1.0 mg to about 2.0 mg on the first day, for instance as a single dose, and the maintenance dose of colchicine on the following day(s) of administration is between about 0.5 mg to about 1.0 mg.

Colchicine formulations described herein, in various embodiments, is administered to a subject in accordance with the aforementioned methods of treatment in an amount sufficient to produce a therapeutic effect. The colchicine formulation is administered in a conventional dosage form prepared by combining the colchicine formulations described herein with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The phrase "therapeutically effective dose or amount" or "effective amount" as used herein is intended to mean an amount of the colchicine formulation that when administered brings about a positive therapeutic response with respect to treatment of a subject with a disease to be treated, e.g., an improvement in the disease can be evidenced by, for example, a delayed onset of clinical symptoms of the disease or condition, a reduction in severity of some or all clinical symptoms of the disease or condition, a slower progression of the disease or condition, an improvement in the overall health or well-being of the subject, or by other parameters well known in the art that are specific to the particular disease.

Therapeutically effective doses of the disclosed compositions, for the inhibition, delay, or reduction of metastases, vary depending upon many different factors, including means of administration, target site, physiological state of the subject, whether the subject is human or an animal, other medications administered, and whether treatment is prophylactic or therapeutic. In certain embodiments the subject is a human, but non-human mammals including transgenic mammals can also be treated. Treatment dosages may be titrated using routine methods known to those of skill in the art to optimize safety and efficacy.

The amount of colchicine administered as a single agent or in combination with at least one other immune modulating therapy is readily determined by one of ordinary skill in the art without undue experimentation given the present disclosure. Factors influencing the mode of administration and the respective amount of colchicine to be administered as a single agent or in combination with at least one other immune modulating therapy include, but are not limited to, the severity of the disease, the history of the disease, the potential for metastases, and the age, height, weight, health, and physical condition of the individual undergoing therapy. Similarly, the amount of colchicine as a single agent or in combination with at least one other immune modulating therapy to be administered will be dependent upon the mode of administration and whether the subject will undergo a single dose or multiple doses of this agent.

Also disclosed and contemplated herein is the use of the colchicine formulations described herein in the manufacture of a medicament for treating a subject with a cancer, wherein the medicament is used in a subject that optionally has been pretreated or is concurrently being treated with at least one other therapy. The term "pretreated" or "pretreatment" as used herein is intended to mean that the subject has received one or more other therapies prior to receiving the medicament comprising the colchicine formulation. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the colchicine formulation. As used herein, the terms "concurrent" or "concomitant" is intended to mean that the subject is receiving one or more other therapies while at the same time receiving the medicament comprising the colchicine formulation. It is not necessary that the subject was a responder to pretreatment with the prior therapy or therapies or a responder to the concurrent therapy or therapies. Thus, the subject that receives the medicament comprising the colchicine formulation could have responded, or could have failed to respond, to pretreatment with the prior therapy, or to one or more of the prior therapies where pretreatment comprised multiple therapies. Examples of other cancer therapies for which a subject can have received pretreatment prior to receiving the medicament comprising the colchicine as a single agent or in combination with at least one other immune modulating therapy include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof.

All of the references cited above, as well as all references cited herein, are incorporated herein by reference in their entireties.

While the compositions, formulations, methods, and uses provided herein have been illustrated and described in detail, above, such illustration and description are to be considered illustrative or exemplary and not restrictive. It will be understood that changes and modifications may be made by those of ordinary skill within the scope and spirit of the following claims. In particular, the present disclosure is intended and contemplated to encompass further embodiments with any combination of features from different embodiments described above and below.

The compositions, formulations, methods, and uses herein are additionally described by way of the following illustrative non-limiting examples that provide a better understanding of these elements and of their many advantages. It should be appreciated by those of skill in the art that the techniques disclosed in the examples that follow represent techniques that function well in the practice of the concepts disclosed herein, and thus are considered to constitute various modes for their practice. However, those of skill in the art should, in light of the present disclosure, appreciate that many changes can be made in the specific embodiments which are disclosed and still obtain a like or similar result without departing from the spirit and scope of the compositions, formulations, methods, and uses described herein.

EXAMPLES

Example 1: Colchicine Sustained Release Tablet

This example illustrates a colchicine sustained release tablet. The tablet uses the ingredients and concentrations shown in Table 1 below.

TABLE 1

| Ingredient | mg/Tablet | Tablet % | Function |
| --- | --- | --- | --- |
| Colchicine | 0.500 | 0.5 | Active Pharmaceutical Ingredient (API) |
| Lactose monohydrate | 59.00 | 59.0 | Filling Agent |
| Pregelatinized Starch | 7.50 | 7.5 | Filling Agent |
| HPMC 6 mPa·s | 1.000 | 1.0 | Binder |
| Purified water[1] | q.s. | q.s. | Diluent for API and Binder |
| Lactose monohydrate | 10.00 | 10.00 | Filling Agent |
| RETALAC ® (lactose monohydrate and HPMC 4000 mPa·s 50/50 w/w %) | 20.00 | 20.00 | Retarding Agent |
| Talc | 1.00 | 1.0 | Glidant |
| Stearic acid 50 | 1.00 | 1.0 | Lubricant |
| Total tablet weight [mg]: | 100.00 | | |

[1]removed within the process

The concentrations may be altered to change certain properties of the formulations, for instance, the dissolution profile. Table 2 shows the ranges for each ingredient.

TABLE 2

| Ingredient | Range | Function |
| --- | --- | --- |
| Colchicine | 0.5-0.75 | Active Pharmaceutical Ingredient (API) |
| Lactose monohydrate | 10-80 | Filling Agent |
| Pregelatinized Starch | 5-50 | Filling Agent |
| HPMC 6 mPa·s | 1-30 | Binder |
| Purified water[1] | q.s. | Diluent for API and Binder |
| Lactose monohydrate | 10-30 | Filling Agent |
| RETALAC ® (lactose monohydrate and HPMC 4000 mPa·s 50/50 w/w %) | 5-40 | Retarding Agent |

TABLE 2-continued

| Ingredient | Range | Function |
|---|---|---|
| Talc | 0.5-5 | Glidant |
| Stearic acid 50 | 0.5-5 | Lubricant |
| Total tablet weight [mg]: | | |

[1] removed within the process

Example 2: Method of Making a Colchicine Sustained Release Tablet

The above ingredients are utilized to make a tablet to the following working directions:

Granulation: The granulation was performed in a Kenwood mixer. The colchicine and HPMC 6 mPa·s were first weighed and separately dissolved into purified water. This solution of HPMC 6 mPa·s was filled in the mixer containing the lactose within 1.5 min followed by a 3 minute mixing time. Subsequently, the dissolved colchicine was sprayed with a filing agent, e.g., lactose monohydrate, under continuous mixing over a period of 15 minutes. These steps were performed at room temperature. The wet granulate was then passed through a 1.0 mm hand sieve. It was then dried in an oven (Haeraeus Group, Hanau, Germany) at 45° C. for 26 h to a residual moisture content of 0.53%, and passed through a 0.8 mm sieve shaker (Erweka AR 400). Density parameters were tested (Engelmann). Bulk density 0.53 g/ml, compacted bulk density 0.67 g/ml, Hausner ratio: 1.26. Rheology: Flow time: 4 sec; slope angle: 23.8°.

Blending: Following the granulation process, the granulate is compounded with a filling agent, e.g., lactose monohydrate, a retarding agent, e.g., RETALAC®, and other excipients, e.g., flow enhancer, glidants, and/or lubricants, to support the tablet compression process. To this end, these ingredients were placed manually through a 0.8 mm sieve and mixed with the granulate in a cube mixer (Erweka GmbH, Heusenstamm, Germany) for 10 minutes. In one embodiment, the glidant used may be talc. In another embodiment, the lubricants used may be Stearic acid. The granulate will then be blended using a suitable mixer.

Compression of Tablets: To form the tablets, a compression force is needed. The mechanical force will define the physical properties of the tablets, especially the crushing strength of the resulting tablet. The mechanical strength interacts with the initial swelling of the tablet and dilution speed of the tablet core. This effect is well known in the art and can be adjusted and controlled during the lifecycle of the product.

Tableting was performed on a Korsch (EK 0) tablet press with a round tableting tool, biconvex, 6 mm in diameter. Average tablet hardness was approximately 100N+/−15N. Tablets measured about 100 mg in mass, friability was not measurable. Breaking strength and hardness were measured with a Erweka Multickeck. Friability was measured with a Erweka Friabilator and a Mettler analytical balance. The dimensions were measured using a Mitutoyo caliper.

Example 3: Measurements of Dissolution Profiles of Sustained-Release Colchicine Formulations The dissolution of the sustained release formulation of colchicine was measured at various time points. The compositions were dissolved in 500 ml of water at 37° C. and stirred continuously over a period of 6 hours. Samples were drawn at several time points to study the kinetics of the dissolution process of the drug substance within the hydrophilic matrix system. Colchicine content in the samples was analyzed using HPLC analysis.

Several batches were tested to determine the optimal dissolution profile for the sustained release formulation. The release can be modified by both the concentration of HPMC or by using different viscosity grades of HPMC, e.g. 1000 mPa·s or 10000 mPa·s. In the batches tested below, the viscosity grade remained constant, however, the concentration of HPMC 4000 mPa·s in the tablet was modified.

Table 3 below summarizes the various compositions that were tested.

TABLE 3

| Material name | Mass [%] | Mass per Tbl. [mg] | Per batch [g] | −0.5% | +0.5% |
|---|---|---|---|---|---|
| Stem granulate: (common for 3 Tablet mixings) | | | | | |
| PE Colchicine | 0.500 | 0.500 | 7.50 | 7.46 | 7.54 |
| Lactose monohydrate EP | 59.000 | 59.000 | 885.00 | 880.6 | 889.4 |
| Pregelatinized Starch USP | 7.500 | 7.500 | 112.50 | 111.94 | 113.06 |
| FB HPMC 6 mPa · s EP/JP/USP | 1.000 | 1.000 | 15.00 | 14.93 | 15.08 |
| Water purified * for Colchicine | 0.000 | 4.000 | 60.00 | 59.70 | 60.30 |
| Water purified * For HPMC | 0.000 | 8.300 | 124.50 | 123.88 | 125.1 |
| Batch 1: Tableting mix 10% RETALAC ® (compression strength = 100N): | | | | | |
| Lactose monohydrate EP (Filling agent ad 100 mg per tablet) | 20.000 | 20.000 | 80.0 | 79.6 | 80.4 |
| PE RETALAC ® (50% lactose/ 50% HPMC 4000 mPa · s) | 10.000 | 10.000 | 40.00 | 39.8 | 40.2 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |

TABLE 3-continued

| Material name | Mass [%] | Mass per Tbl. [mg] | Per batch [g] | −0.5% | +0.5% |
|---|---|---|---|---|---|
| Batch 2: Tableting mix 15% RETALAC ® (compression strength = 100N): | | | | | |
| Lactose monohydrate EP (Filling agent ad 100 mg per tablet) | 15.000 | 15.000 | 60.00 | 59.7 | 60.3 |
| PE RETALAC ® (50% lactose/ 50% HPMC 4000 mPa · s) | 15.000 | 15.000 | 60.00 | 59.7 | 60.3 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 3: Tableting mix 20% RETALAC ® (compression strength = 100N): | | | | | |
| Lactose monohydrate EP (Filling agent ad 100 mg per tablet) | 10.000 | 10.000 | 40.00 | 79.6 | 80.4 |
| PE RETALAC ® (50% lactose/ 50% HPMC 4000 mPa · s) | 20.000 | 20.000 | 80.00 | 79.6 | 80.4 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 4: Tableting mix 30% RETALAC ® (compression strength = 50N and 130N): | | | | | |
| Lactose monohydrate EP (Filling agent ad 100 mg per tablet) | 0.000 | 0.000 | 00.00 | 0.0 | 0.0 |
| PE RETALAC ® (50% lactose/ 50% HPMC 4000 mPa · s) | 30.000 | 30.000 | 120.00 | 119.40 | 120.60 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |
| Batch 5: Tableting mix 0% RETALAC ® (compression strength = 100N): | | | | | |
| Lactose monohydrate EP (Filling agent ad 100 mg per tablet) | 30.000 | 30.000 | 120.00 | 119.40 | 120.60 |
| PE RETALAC ® (50% lactose/ 50% HPMC 4000 mPa · s) | 0.000 | 00.000 | 00.00 | 0.0 | 0.0 |
| Talc EP/JP | 1.000 | 1.000 | 4.00 | 3.98 | 4.02 |
| Stearic acid 50 EP | 1.000 | 1.000 | 4.00 | 3.98 | 4.02 |
| Total tablet weight: | 100.000 | 100.000 | | | |

The dissolution profiles of the various batches are provided in Tables 4-6 and FIGS. 1-4. In particular, the dissolution profile for Batches 1-3 is summarized in Table 4 and FIG. 1. The profile for Batch 1 shows approximately a 92% release within about 30 minutes, followed by a constant release. Complete dissolution occurred after 2 hours. Batch 2 shows approximately a 83% release within about 30 minutes, followed by a constant release. Complete dissolution occurred after 2 hours. Batch 3 shows approximately a 74% release within about 30 minutes, followed by a constant release. Complete dissolution occurred after 2 hours.

TABLE 4

| Concentration Retardant | Sample | Hour 0 | Hour 0.5 | Hour 1 | Hour 2 | Hour 4 |
|---|---|---|---|---|---|---|
| 10% RETALAC ® | 1. | | 90.6 | 98.1 | 99.1 | 98.9 |
| | 2. | | 93.7 | 97.6 | 97.5 | 97.6 |
| | 3. | | 98.6 | 99.3 | 99.5 | 99.8 |
| | 4. | | 93.7 | 97.5 | 98.1 | 98.2 |
| | 5. | | 89.9 | 93.7 | 93.7 | 93.8 |
| | 6. | | 89.6 | 97.2 | 97.5 | 97.6 |
| | Mean | 0 | 92.7 | 97.2 | 97.6 | 97.7 |
| 15% RETALAC ® | 1. | | 75.1 | 89.2 | 95.9 | 96.0 |
| | 2. | | 74.5 | 91.3 | 95.0 | 94.9 |
| | 3. | | 85.7 | 99.1 | 100.3 | 100.2 |
| | 4. | | 86.9 | 98.2 | 100.1 | 99.3 |
| | 5. | | 84.7 | 93.9 | 94.6 | 94.3 |
| | 6. | | 90.7 | 96.0 | 95.7 | 96.1 |
| | Mean | 0 | 82.9 | 94.6 | 96.9 | 96.8 |
| 20% RETALAC ® | 1. | | 68.1 | 87.7 | 97.8 | 97.8 |
| | 2. | | 62.0 | 83.2 | 95.2 | 96.3 |
| | 3. | | 85.4 | 95.2 | 98.2 | 98.3 |
| | 4. | | 76.6 | 94.7 | 97.2 | 96.9 |
| | 5. | | 71.8 | 94.5 | 103.5 | 103.1 |
| | 6. | | 80.6 | 95.4 | 99.0 | 98.9 |
| | Mean | 0 | 74.1 | 91.8 | 98.5 | 98.6 |

Figure 1:
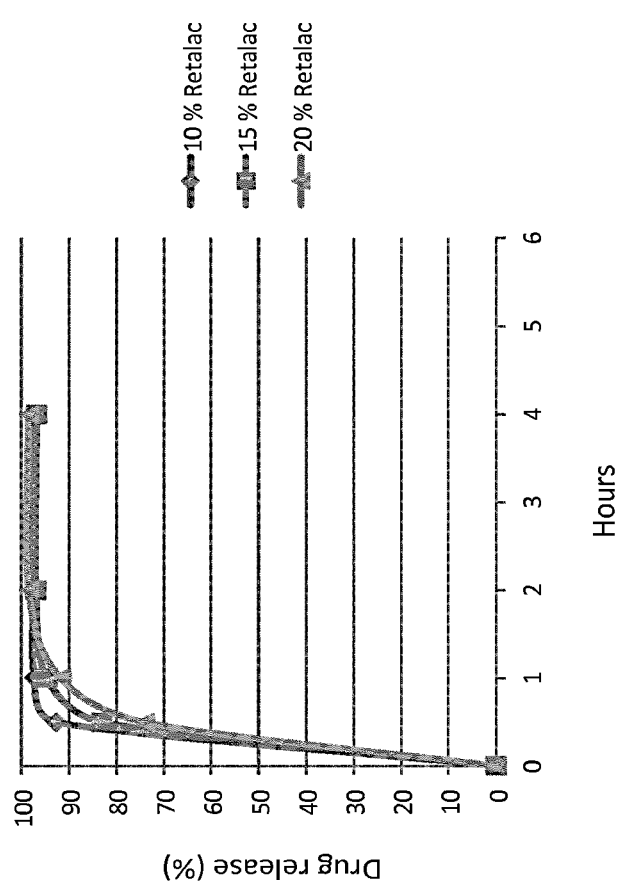
FIG. 1 shows the dissolution profiles for colchicine sustained-release formulations containing 10%, 15% and 20%, respectively, of an exemplary retarding agent.
Figure 2:
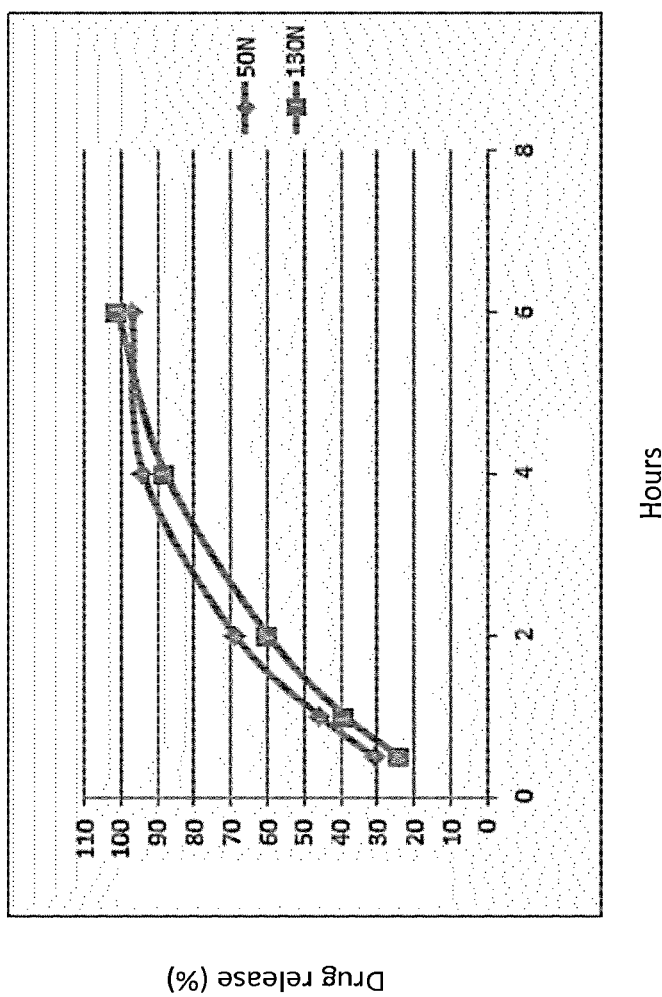
FIG. 2 shows the dissolution profiles for colchicine sustained-release formulation containing 30% of an exemplary retarding agent and a tablet hardness of 50N and 130N, respectively.
Figure 3:
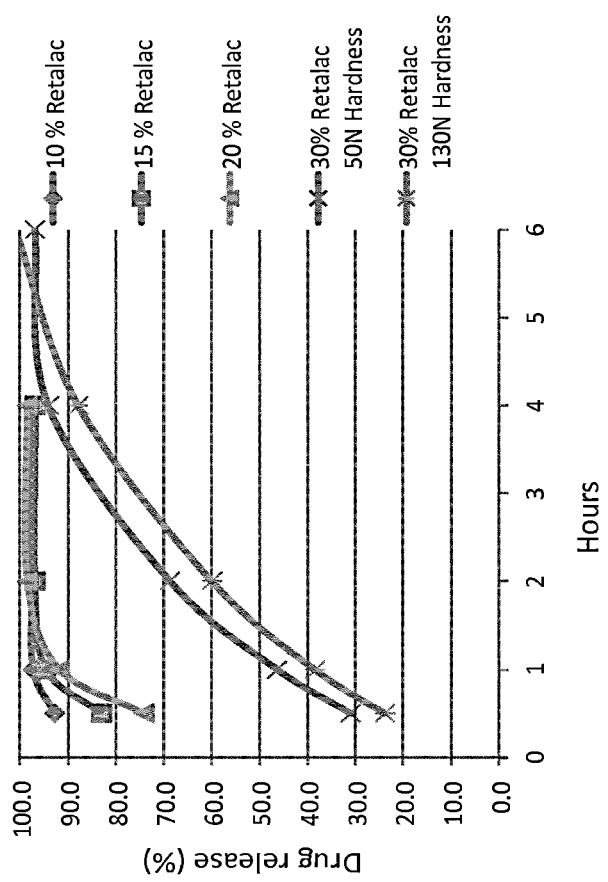
FIG. 3 shows the dissolution profiles for colchicine sustained-release formulations according to FIGS. 1 and 2.

The dissolution profile for Batch 4 is summarized in Table 5 and FIG. 2. Batch 4A shows approximately a 30% release within about 30 minutes, followed by a constant release. Complete dissolution occurred after 6 hours. Batch 4B shows approximately a 23% release within about 30 minutes, followed by a constant release. Complete dissolution occurred within 6 hours. In this example, a difference in tablet hardness results in a difference in release rates. FIG. 3 shows the dissolution profiles for Batches 1-4.

TABLE 5

| Concentration Retardant | Sample | Hour 0.5 | Hour 1 | Hour 2 | Hour 4 | Hour 6 |
|---|---|---|---|---|---|---|
| (A) 30% | No.1 | 30.5 | 47.1 | 70.7 | 96.5 | 96.9 |
| | No.2 | 34.5 | 49.3 | 70.6 | 95 | 98 |

TABLE 5-continued

| Concentration Retardant | Sample | Hour 0.5 | Hour 1 | Hour 2 | Hour 4 | Hour 6 |
|---|---|---|---|---|---|---|
| RETALAC® 50N Hardness (B) 30% RETALAC® 130N Hardness | No.3 | 27.8 | 42.6 | 64.6 | 90.9 | 95.8 |
| | | 30.9 | 46.3 | 68.6 | 94.1 | 96.9 |
| | No.4 | 22.5 | 37.1 | 54.9 | 81.2 | 92.5 |
| | No.5 | 25.9 | 42 | 67.1 | 94.5 | 108.7 |
| | No.6 | 23.3 | 36.5 | 57.8 | 87.9 | 101.8 |
| | | 23.9 | 38.5 | 59.9 | 87.9 | 101.0 |

Figure 4:
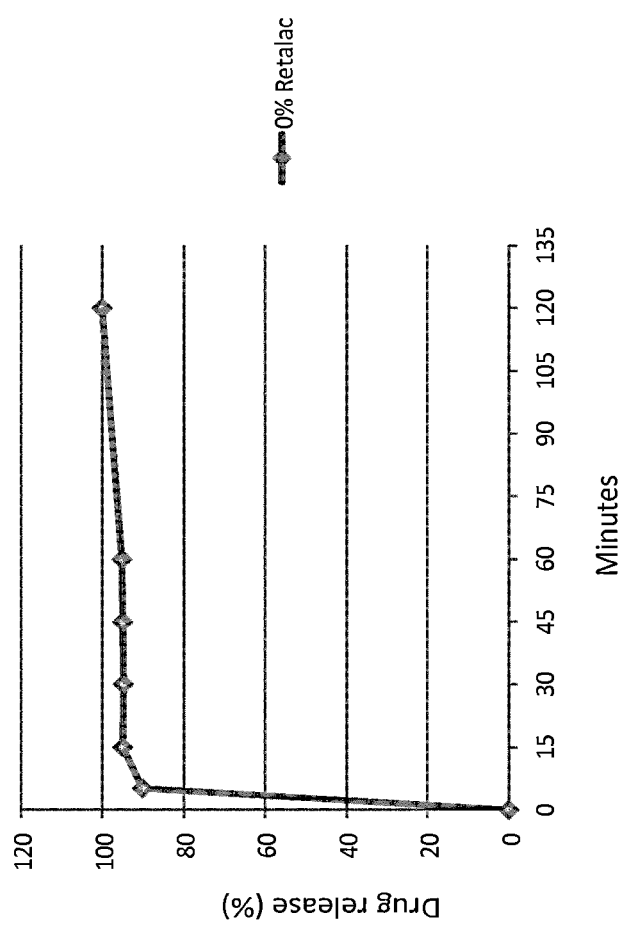
FIG. 4 shows the dissolution profile for a colchicine sustained-release formulation containing 0% of an exemplary retarding agent.

The dissolution profile for Batch 5 is summarized in Table 6 and FIG. 4. Batch 5 represents the immediate release version of the composition. The profile for Batch 5 shows a 90% release within 5 minutes. Complete dissolution occurred within 2 hours.

TABLE 6

| Concentration Retardant | Sample | min 0 | min 5 | min 15 | min 30 | min 45 | min 60 | min 120 |
|---|---|---|---|---|---|---|---|---|
| 0% RETALAC® | 1. | | 92.2 | 96.8 | 96.8 | 96.9 | 97.2 | |
| | 2. | | 96.7 | 100.6 | 99.9 | 100.3 | 100.7 | |
| | 3. | | 94.7 | 100.8 | 100.5 | 100.9 | 101.1 | |
| | 4. | | 86.5 | 92.7 | 92.9 | 93.1 | 93.3 | |
| | 5. | | 85.6 | 91 | 91.7 | 91.4 | 91.8 | |
| | 6. | | 84.5 | 88.1 | 87.1 | 87.1 | 87.5 | |
| | Mean | 0 | 90.0 | 95.0 | 94.8 | 95.0 | 95.0 | 100 |

Table 7 below summarizes another batch, Batch 6, that was tested.

Figure 5:
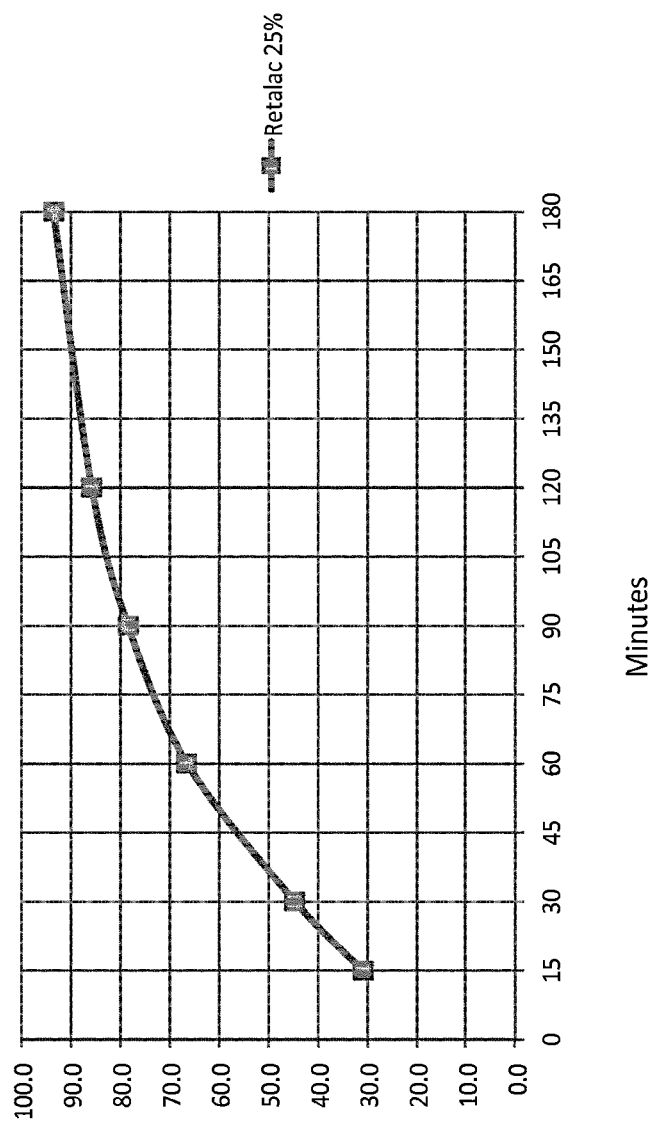
FIG. 5 shows the dissolution profile for a colchicine sustained-release formulation containing 25% of an exemplary retarding agent.

The dissolution profile for Batch 6 is summarized in Table 7 and FIG. 5A. Batch 6 represents a sustained release version of the composition. The profile for Batch 6 in FIG. 5A shows about a 45% release within 30 minutes, about a 65% release in 60 minutes, and about a 80% release in 90 minutes. Complete dissolution occurs within about 2 hours.

Figure 7:
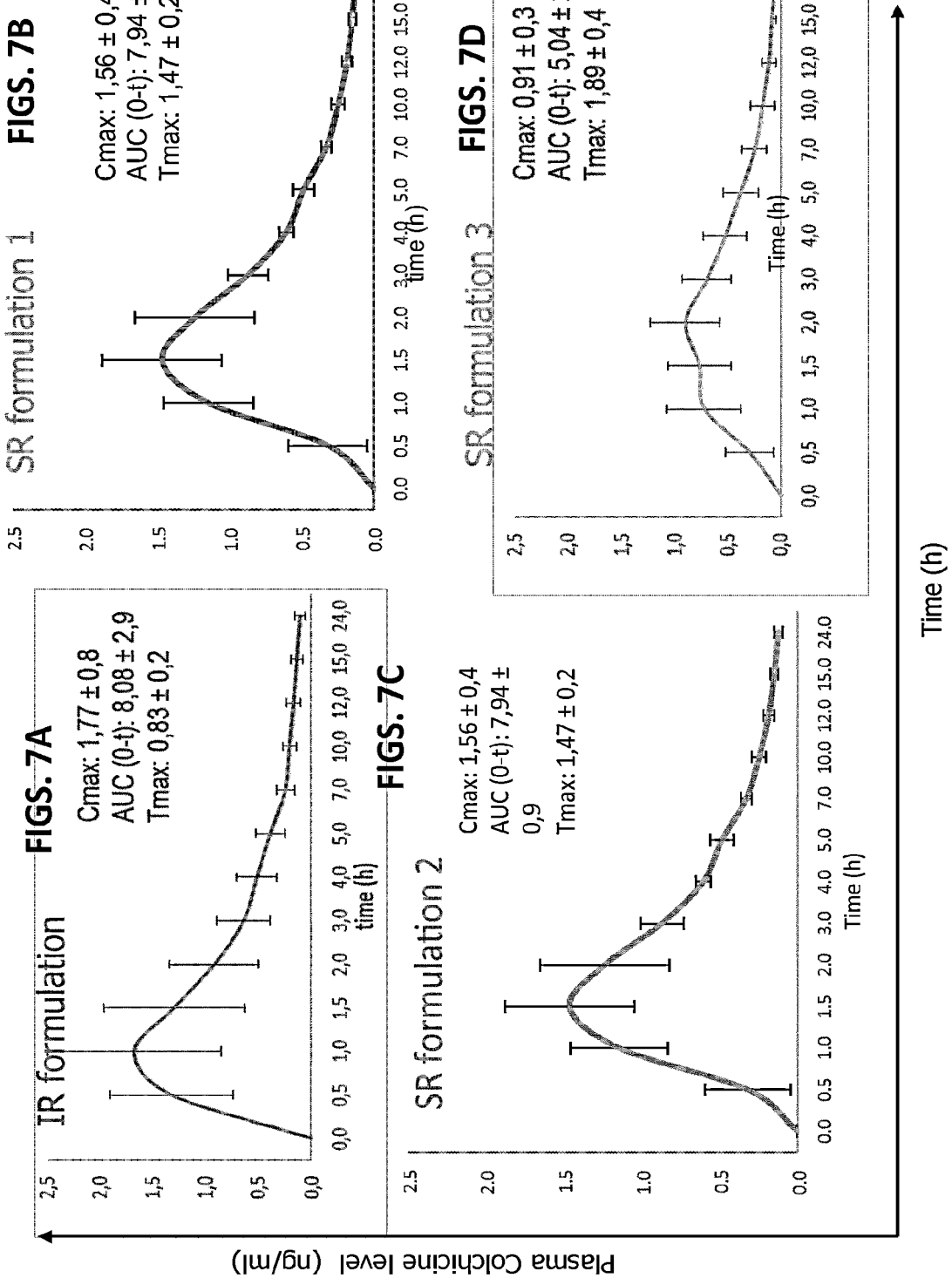

Batch 4 was further modified by altering the concentration of retarding agent (i.e. RETALAC®) in the composition (RETALAC® 0%, 23.3%, 26.6% or 30%). The dissolution profiles of the four compositions are shown in FIG. 6. As shown in FIG. 6, the composition with 23.3% RETALAC® shows about a 65% release within 30 min, about a 80% release in 60 min, and about a 90% release in 90 min. Complete dissolution occurs within about 120 min. As further shown in FIG. 6, the composition with 26.6% RETALAC® shows about a 55% release within 30 min, about a 75% release in 60 min, and about a 85% release in 90 min. Complete dissolution occurs within about 180 min. As further shown in FIG. 6, the composition with 30% RETALAC® shows about a 40% release within 30 min, about a 55% release in 60 min, and about a 70% release in 90 min. Complete dissolution occurs in more than about 180 min. As further shown in FIG. 6, the composition with 0% RETALAC®, i.e., immediate release composition, shows complete dissolution within about 15 min. FIG. 7A, FIG. 7B, FIG. 7C, FIG. D, and FIG. 8 show plasma colchicine levels (ng/mL) as a function of time (hrs) for colchicine formulations according to FIG. 6.

As mentioned previously, the release profile of the sustained release composition can be changed to a specific or

TABLE 7

| Material name | Mass [%] | Mass per Tbl. [mg] | Per batch [g] | Range for variation | | Weighting Tolerance |
|---|---|---|---|---|---|---|
| PE Colchicine | 0.550 | 0.550 | 5.5 | | | 0.5% |
| lactose monohydrate EP | 58.950 | 58.950 | 589.50 | | | 1% |
| Pregelatinized Starch USP | 7.500 | 7.500 | 75.00 | | | 1% |
| FB HPMC 6 mPa · s EP/JP/USP | 1.000 | 1.000 | 10.00 | | | 1% |
| Water purified * for Colchicine | 0.000 | 4.000 | 40.00 | | | 1% |
| Water purified * For HPMC | 0.000 | 8.300 | 83.00 | | | 1% |
| Tableting mix 25% RETALAC ® (compression strength = 55N): | | | | | | |
| lactose monohydrate EP (Filling agent ad 100 mg per tablet) | 5.00 | 5.00 | 50.00 | 2.5% | 10% | 1% |
| PE RETALAC ® (50% lactose/ 50% HPMC 4000 mPa · s) | 25.00 | 25.00 | 250.00 | 20% | 27.5% | 1% |
| Talc EP/JP | 1.000 | 1.000 | 10.00 | | | 1% |
| Stearic acid 50 EP | 1.000 | 1.000 | 10.00 | | | 1% |
| Total tablet weight: | 100.000 | 100.000 | 1,000.00 | | | |
| Related Substances | NMT 2.5% | | | | | |
| N-Deacetyl-N-formyl-colchicine (imp A) | NMT 1% | | | | | |
| unknown impurities | NMT 3.5% | | | | | |
| Total impurities | | | | | | | desired target release by adjusting the amount of retarding agent, i.e., RETALAC®, as well as tablet hardness. The release depends upon a variety of factors, including erosion of the outer layer of colchicine, i.e., the immediate release portion, as well as diffusion of the inner layer of colchicine, i.e., the sustained release portion. Since the percentage of colchicine is low in the sustained release formulation and the tablets are small, this balance between erosion and diffusion is very sensitive and has to be fine-tuned to reach a very specific dissolution profile.

Example 4: Therapeutic Effects of Colchicine in Subjects with Cancer

To assess the therapeutic effects of a sustained release formulation in subjects with or in subjects with an increased risk of cancer, a prospective randomized observer blinded end-point trial was conducted to determine whether adding 0.5 mg/day of colchicine to standard anti-cancer therapies inhibits, delays, or reduces tumor growth or metastases in a cancer subject.

A sufficient amount of subjects with cancer or in risk of cancer are randomized to long-term low dose sustained release colchicine or to standard therapy alone. Cancer incidence, morbidity and mortality are analyzed in regular intervals. Subjects in the colchicine arm have a significantly lower cancer incidence and mortality than subjects not treated with colchicine.

Example 5: Anti-Tumor Effects of Colchicine in Animals

A sufficient amount of specimen of a suitable animal species are included in this study utilizing commonly used tumor models. A therapeutically effective amount of colchicine is administered to the test animals. Placebo is administered to a control group. Tumor growth is induced in all animals. In animals treated with colchicine, tumor growth is prevented and/or reduced as compared to the control group.

Example 6: Anti-Tumor Effects of Colchicine In Vitro

A suitable in vitro model for studying the anti-tumor effects of drugs is utilized for this test. Such a test may include commonly used tumor cell lines with or without combination with cultivated PBMCs. Colchicine inhibits or reduces growth of tumor cell lines upon incubation with therapeutically effective amount of colchicine and/or cultivation with PBMCs pretreated with a therapeutically effective amount of colchicine.

Many modifications and other embodiments of the embodiments set forth herein will come to mind to one skilled in the art to which these embodiments pertain having the benefit of the teachings presented in the foregoing descriptions and the associated drawings. Therefore, it is to be understood that the presently disclosed features are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method for inhibiting, delaying, or reducing tumor growth or metastases or both tumor growth and metastases in a subject diagnosed with or suffering from cancer, comprising administering to the subject a sustained release formulation comprising a homogeneous mixture of:
    (a) between 0.1 mg to 0.60 mg of colchicine or a pharmaceutically acceptable salt thereof;
    (b) a binder, wherein the binder is hydroxypropyl methylcellulose (HPMC) 6 mPa·s;
    (c) a retarding agent, wherein the retarding agent is a spray agglomerated blend of equal parts by weight of HPMC with a viscosity grade of 4000 mPa·s and lactose monohydrate; and
    (d) at least one pharmaceutically acceptable excipient, wherein the sustained release formulation is a tablet.

2. The method of claim 1, wherein colchicine induces anti-tumor responses.

3. The method of claim 1, wherein colchicine inhibits IL-1β mediated signaling.

4. The method of claim 1, wherein colchicine inhibits inflammation activation.

5. The method of claim 1, wherein colchicine inhibits release of TNF-α and IL-10.

6. The method of claim 1, wherein the inhibition, delay, or reduction of metastases occurs independently of primary tumor growth inhibition, delay, or reduction.

7. The method of claim 1, wherein colchicine is included in an amount between about 0.5 mg and about 0.60 mg.

8. The method of claim 1, wherein colchicine is included in an amount of 0.55 mg.

9. The method of claim 1, wherein the cancer is one or more of carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulvar cancer, thyroid cancer, and head and neck cancer.

10. A method for inhibiting, delaying, or reducing tumor growth or metastases or both tumor growth and metastases in a subject diagnosed with or suffering from cancer, comprising administering to the subject a sustained release formulation comprising a homogeneous mixture of:
    (a) between 0.1 mg to 0.60 mg of colchicine or a pharmaceutically acceptable salt thereof;
    (b) a binder, wherein the binder is hydroxypropyl methylcellulose (HPMC) 6 mPa·s;
    (c) a retarding agent, wherein the retarding agent is a spray agglomerated blend of equal parts by weight of HPMC with a viscosity grade of 4000 mPa·s and lactose monohydrate; and
    (d) at least one pharmaceutically acceptable excipient, wherein the sustained release formulation is a tablet, and an effective amount of at least one other immune modulating therapy.

11. The method of claim 10, wherein colchicine induces anti-tumor responses.

12. The method of claim 10, wherein colchicine inhibits IL-1β mediated signaling.

13. The method of claim 10, wherein colchicine inhibits release of TNF-α and IL-10.

14. The method of claim 10, wherein colchicine inhibits inflammation activation.

15. The method of claim 10, wherein the inhibition, delay, or reduction of metastases occurs independently of primary tumor growth inhibition, delay, or reduction.

16. The method of claim 10, wherein colchicine is included in an amount between about 0.5 mg and about 0.60 mg.

17. The method of claim 10, wherein colchicine is included in an amount of 0.55 mg.

18. The method of claim 10, wherein the cancer is one or more of carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulvar cancer, thyroid cancer, and head and neck cancer.

19. The method of claim 10, wherein the immune modulating agent is one or more of interleukins, cytokines, chemokines, and antagonists of immune checkpoint blockades.

20. The method of claim 10, wherein the immune modulating therapy is a cancer therapy.

21. The method of claim 20, wherein the cancer therapy is one or more of surgery or surgical procedures, radiation therapy, and chemotherapy.

22. The method of claim 10, wherein colchicine and the immune modulating agent or immune modulating therapy are administered separately or concurrently.

* * * * *